United States Patent
Kricek et al.

(10) Patent No.: US 6,610,297 B1
(45) Date of Patent: *Aug. 26, 2003

(54) PEPTIDE IMMUNOGENS FOR VACCINATION AGAINST AND TREATMENT OF ALLERGY

(75) Inventors: Franz Kricek, Biedermannsdorf (AT); Beda Stadler, Bern (CH)

(73) Assignee: Novartis AG, Basel (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/125,641

(22) PCT Filed: Feb. 28, 1997

(86) PCT No.: PCT/EP97/01013

§ 371 (c)(1),
(2), (4) Date: Aug. 21, 1998

(87) PCT Pub. No.: WO97/31948

PCT Pub. Date: Sep. 4, 1997

(30) Foreign Application Priority Data

Mar. 1, 1996 (GB) .................................. 9604412
Aug. 22, 1996 (GB) .................................. 9617702

(51) Int. Cl.[7] ................ A61K 39/00; A61K 39/44; A61K 39/395; C07K 7/06; C07K 7/08
(52) U.S. Cl. ................ 424/178.1; 424/131.1; 424/139.1; 424/185.1; 530/326; 530/327; 530/328; 530/387.2; 530/387.9
(58) Field of Search .................. 424/131.1, 139.1, 424/178.1, 185.1; 530/324, 327, 387.9, 328, 387.2

(56) References Cited

U.S. PATENT DOCUMENTS

| | | | |
|---|---|---|---|
| 4,161,522 A | 7/1979 | Hamburger | 424/177 |
| 4,171,299 A | 10/1979 | Hamburger | 260/112.5 |
| 4,223,016 A | 9/1980 | Roy et al. | 424/177 |
| 4,892,827 A | 1/1990 | Pastan et al. | 435/193 |
| 5,258,289 A | 11/1993 | Davis et al. | 435/69.6 |
| 5,342,924 A | 8/1994 | Chang | 530/387.9 |
| 5,449,760 A | 9/1995 | Chang | 530/387.3 |
| 5,759,551 A | 6/1998 | Ladd et al. | 424/198.1 |
| 5,965,709 A | * 10/1999 | Presta et al. | 530/387.3 |

FOREIGN PATENT DOCUMENTS

| | | |
|---|---|---|
| EP | 0 102 634 | 6/1988 |
| EP | 0 269 455 | 6/1988 |
| EP | 0 396 505 A2 | 4/1990 |
| EP | 0 477 231 | 4/1992 |
| EP | 0 592 230 | 4/1994 |
| EP | 0 287 361 | 6/1994 |
| EP | 0 955 311 A2 | 4/1999 |
| WO | WO 88/00204 | * 1/1988 |
| WO | WO 88/06040 | 8/1988 |
| WO | WO 89/03430 | 4/1989 |
| WO | WO 89/04834 | 6/1989 |
| WO | WO 91/11456 | 8/1991 |
| WO | WO 91/19001 | 12/1991 |
| WO | WO 92/13081 | 8/1992 |
| WO | WO 93/04173 | * 3/1993 |
| WO | WO 93/05810 | 4/1993 |
| WO | WO 93/11153 | 6/1993 |
| WO | WO 94/24278 | 10/1994 |
| WO | WO 94/25060 | 11/1994 |
| WO | WO 94/26723 | 11/1994 |
| WO | WO 95/10532 | 4/1995 |
| WO | WO 95/14779 | 6/1995 |
| WO | WO 95/20606 | 8/1995 |
| WO | WO 95/26365 | 10/1995 |
| WO | WO96/01643 | 1/1996 |
| WO | WO 96/12740 | 5/1996 |
| WO | WO 98/24808 | 6/1998 |
| WO | WO 99/66957 | 12/1999 |

OTHER PUBLICATIONS

Russell, M.A. and Darzins, A. Molec. Microbiol. 13(6):973–985, 1994.*
Aujame et al., Tibetch, vol. 15, "Phage display and antibody engineering: a French overview," pp. 155–157, (May 1997).
Chang, Tse Wen, Nature Biotechnology, vol. 18, "The pharmacological basis of anti–IgE therapy," pp. 157–162, (Feb. 2000).
Fishman et al., Eur. J. Immunol., vol. 27, "Targeted elimination of cells expressing the high–affinity receptor for IgE (FcεRI) by a *Psuedomonas* exotoxin–based chimeric protein," pp. 486–494, (1997).
Greenspan, Neil S., Nature Biotechnology, vol. 15, "Reflections on Internal Images," pp. 123–124, Feb. 1997).
Junghans, R.P., Tibtech, vol. 15, "Next–generation Fc chimeric proteins: avoiding immune system interactions," pp. 155, (May 1997).
Knutti–Muller et al., Allergy, vol. 41, "Human IgE Synthesis in vitro," pp. 457–467, (1986).
Miescher et al., Int. Arch. Allergy Immunol., vol. 105, "Domain–Specific Anti–IgE Antibodies Interfere with IgE Binding to FcεRII," pp. 75–82, (1994).
Padlan, et al., Molecular Immunology, vol. 23(10), "A Model of the Fc of Immunoglobulin E," pp. 1063–1075, (1986).
Rudolf, et al., The Journal of Immunology, vol. 160(7), "Epitope–Specific Antibody Response to IgE by Mimotope Immunization," pp. 3315–3321, (1998).

(List continued on next page.)

*Primary Examiner*—David Saunders
*Assistant Examiner*—Mary Beth Tung
(74) *Attorney, Agent, or Firm*—David E. Wildman

(57) ABSTRACT

Disclosed are compositions for treating allergies that include either BSW17 mimotope peptides or antibodies raised against BSW17 mimotope peptides. Also disclosed are methods for the treatment of allergies which involve administration of BSW17 mimotope peptides or the administration of antibodies raised against BSW17 mimotope peptides.

16 Claims, 19 Drawing Sheets

(1 of 19 Drawing Sheet(s) Filed in Color)

OTHER PUBLICATIONS

Stadler et al., Prog. Allergy Clin. Immunol., vol. 4, "Anti-IgE Vaccination," pp. 339–342, (1997).
Watts, Colin, Nature, vol. 388, "Inside the gearbox of the dendritic cell, " pp. 724–725, (Aug. 21, 1997).
Derwent Abstract 89–013386/02, I. Shuichi et. al., JP 63290899, Nov. 28, 1988.
Derwent Abstract 95–265243/35, Hurpin et al., FR 2715304, Jul. 28, 1995.
Laing, Peter et al., The Lancet, "Vaccination against asthma", vol. 344, pp. 1639 (1994).
Nakajiam, K. et al., Allergy, "Effect of anti–IgE antibodies on IgE binding to CD 23", vol. 44, pp. 187–191 (1989).
Rudolf, Michael P. et al., N.Y. Acad. Sci, Conference, B–Lymphocytes and Autoimmunity (May 21–26, 1996), Specific anti–Human IgE Response by Mimotope Immunisation (abstract).
Derwent Abstracts, 118:145935 (1993), FEBS L., vol. 314, pp. 229–231 (1992) Nio, N., et al. (Abstract only).
Chemical Abstracts, 95407737, (MEDLINE)(1995), Allergy, vol. 50, pp. 243–8 Czech, N., et al. (Abstract only).
Chemical Abstracts, 95328672 (MEDLINE)(1995), Allergy, vol. 50, pp. 119–125. Yu, Y., et al. (Abstract only).
Chemical Abstracts, 125:294362 (1996), Molec. Microbiol., vol. 22, pp. 161–173 Aim, R.A., et al. (Abstract only).
Chemical Abstracts, 126–30040 (1996), Molec. Diversity, vol. 2, pp. 13–18 Peletskaya, E.N., et al. (Abstract only).
Stadler, B.M. et al., Int. Arch Allergy Immunol., vol. 113, (Conference of Sep. 6–11, 1997 in Salzburg, Austria) pp. 216–218 (1997).
Stanworth, D.R. et al., The Lancet, vol. 336, "Allergy treatment with a peptide vaccine", pp. 1279–1281 (1990).
Chemical Abstracts, 97:209518 (1982), EMBO J., vol. 1, pp 655–660 Flanagan, T.G., et al (Abstract only).
Chemical Abstracts, 98:120542 (1982), EMBO J., vol. 1, pp. 1539–1544 Ueda, S., et al. (Abstract only).
Chemical Abstracts, 98:155829 (1983), Nucl. Ac. Res., vol. 11, pp. 719–726 Seno, M, et al. (Abstract only).
Chemical Abstracts, 102:216173 (1985), Immunogenet. (Proc. Int. Symp. 1983) (1984), pp. 227–238 Miki, T., et al. (Abstract only).
Chemical Abstracts, 107:234420 (1987), J. Clin. Lab. Anal., vol. 1, pp. 251–261 Spiegelberg, H.L., et al. (Abstract only).
Chemical Abstracts, 109:90892 (1988), Peptide Chem., vol. 1987, pp. 765–8 Nio, N., et al. (Abstract only).

* cited by examiner

BSW17 MIMOTOPE-BASED IMMUNOTHERAPY

CH2 CH3 CH4

BSW17 ANALOGUE: NEUTRALIZING, NON ANAPHYLACTOGENIC, IgE STRIPPING, INHIBITS IgE SYTHESIS

FIG. 4

BINDING OF A CHEMICALLY SYNTHESIZED BSW17
MIMOTOPE PEPTIDE TO BSW17

30 nM Kri-13.SYN-RHODOL GREEN,
150 mM NaPi/pH=6.8
Kd = 24.5 +/- 12.5 nM

[BSW17] µM

FIG.7

RECOGNITION OF CYCLIC BSW17 MIMOTOPE GEFCINHRGYWVCGDPA-KLH
(BSS) CONJUGATE (SDS 236) AND Fcε (500-509)-KLH (BSS)
CONJUGATE (SDS 237) BY BSW17

FIG.8a

RECOGNITION OF VARIOUS BSW17 MIMOTOPE CONJUGATES BY BSW17

FIG.8b

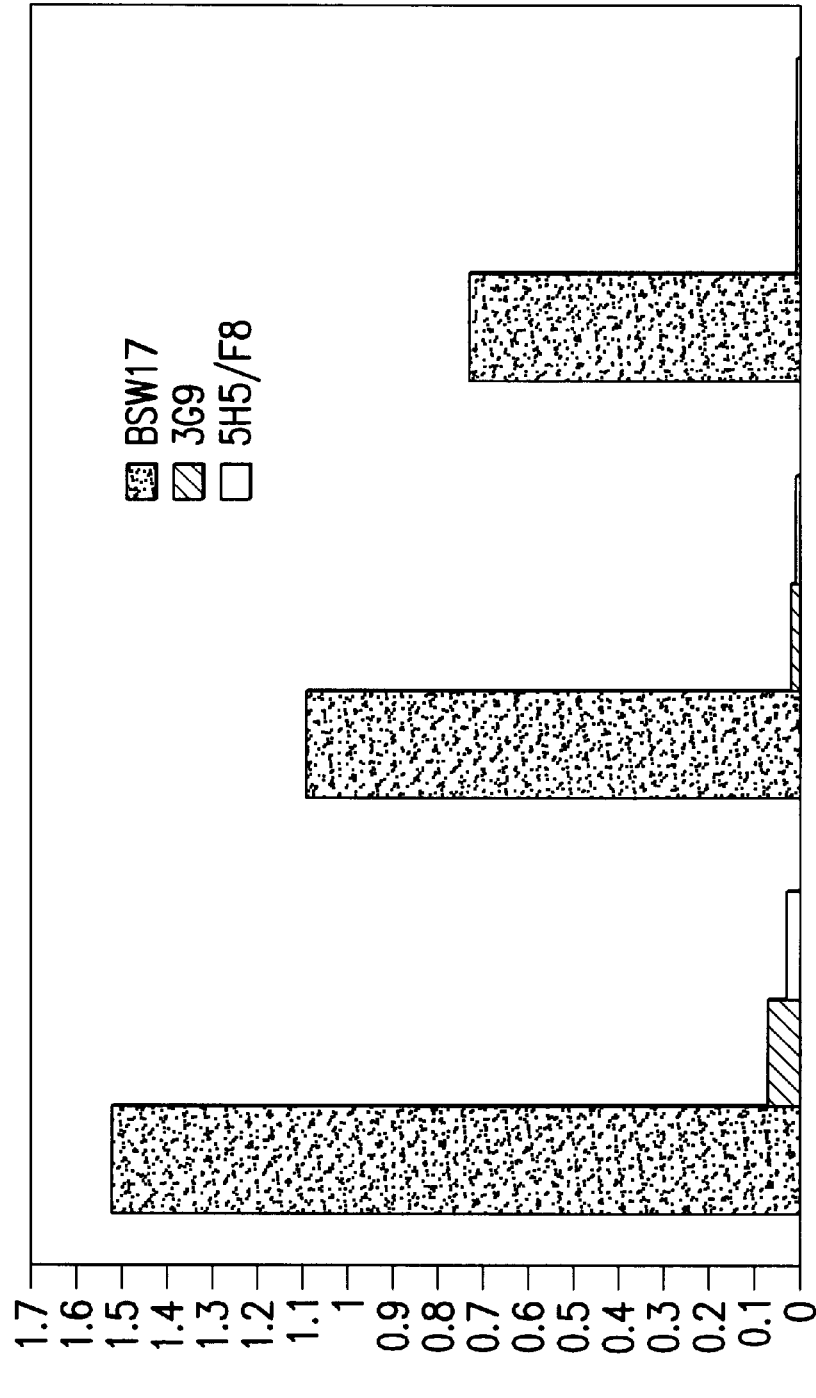

SPECIFIC RECOGNITION OF BSW17 MIMOTOPE CONJUGATES [KLH (DC); Lys] BY BSW17 n.d. = NOT DETERMINED

FIG. 9b

ANTI HUMAN IgE IMMUNE RESPONSE INDUCED IN RABBITS AFTER IMMUNIZATION WITH BSW17 MIMOTOPE CONJUGATES (1)

FIG.10a

ANTI HUMAN IgE IMMUNE RESPONSE INDUCED IN RABBITS AFTER
IMMUNIZATION WITH BSW17 MIMOTOPE CONJUGATES (2)

FIG.10b

SERUM TITERS OF ANTI BSW17 MIMOTOPE ANTIBODIES
GENERATED IN RABBITS BY IMMUNIZATION

IMMUNIZATION OF RABBITS WITH BSW17 MIMOTOPE-KLH CONJUGATE SDS 213

FIG.11a

SERUM TITERS OF ANTI BSW17 MIMOTOPE ANTIBODIES
GENERATED IN RABBITS BY IMMUNIZATION

IMMUNIZATION OF RABBITS WITH BSW17 MIMOTOPE-KLH CONJUGATE SDS 214

COMPETITION OF ANTI BSW17 MIMOTOPE SERUM WITH BSW17 FOR IgE BINDING (Bar chart: O.D.405 vs SUS-11 IgE-R2 (SDS 214) SERUM 1:50)
- 0 μg BSW 17: ~0.42
- 5 μg BSW 17: ~0.12

PEPTIDE IMMUNOGENS FOR VACCINATION AGAINST AND TREATMENT OF ALLERGY

FIELD

This is a 371 of PCT/EP97/01 013, filed Feb. 28, 1997.

The present invention relates to peptide immunogens, and is directed to inhibition of interactions which would normally cause the triggering of mast cells and basophils induced by cell-bound IgE linked to,an allergen resulting in the release of pharmacologically active mediators as well as the de novo synthesis of cytokines involved in the regulation of allergic and inflammatory reactions. It concerns immunogenic molecules including a moiety of a BSW 17 mimotope peptide and their use.

BACKGROUND

Allergic symptoms are brought about through the release of pharmacologically active mediators, notably histamine, leukotrienes and enzymes, from cells into surrounding tissue and vascular structures. These mediators are normally stored or synthesized de novo in special cells known as mast cells and basophil granulocytes. Mast cells are dispersed throughout animal tissue whilst basophils circulate within the vascular system. These cells synthesize and store mediators within the cell, unless a specialized sequence of events occurs to trigger its release.

The role of immunoglobulin E (IgE) antibodies in mediating allergic reactions is well known. IgE is a complex arrangement of polypeptide chains which, as in other immunoglobulins consists of two light and two heavy chains linked together by disulphide bonds in a "Y" shaped configuration. Each light chain has two domains, one variable ($V_L$) domain linked to a domain with a relatively invariant amino acid sequence termed a constant domain ($C_L$). Heavy chains, by contrast, have one variable domain ($V_H$) and in the case of IgE, four constant domains ($C_H1$, $C_H2$, $C_H3$, $C_H4$, also known as C$\epsilon$1, C$\epsilon$2, C$\epsilon$3, C$\epsilon$4). The two "arms" of the antibody are responsible for antigen binding, having regions where the polypeptide structure varies, and are termed Fab' fragments or F(ab')2, which respresents two Fab' arms linked together by disulphide bonds. The "tail" or central axis of the antibody contains a fixed or constant sequence of peptides and is termed the Fc fragment. The Fc fragment contains interactive sites which enable the antibody to communicate with other immune system molecules or cells by binding to their Fc receptors.

Fc receptors are molecules which bind specifically to active molecular sites within immunoglobulin Fc regions. Fc receptors may exist as integral membrane proteins within a cell's outer plasma membrane or may exist as free "soluble" molecules which freely circulate in blood plasma or other body fluids. In the human system, high affinity binding of IgE to the receptor Fc$\epsilon$RI is accomplished by a complex protein-protein interaction involving various parts of the third heavy chain constant region domain (C$\epsilon$3) of IgE, and the membrane-proximal, immunoglobulin-like domain ($\alpha$2) of the Fc$\epsilon$RI$\alpha$ subunit.

Although residues within the C$\epsilon$3 domain of the IgE heavy chain constant region, and regions belonging to the $\alpha$2 domain of the Fc$\epsilon$RI$\alpha$ receptor, have been identified which are important for binding, the detailed mechanism of the binding process are still obscure. Experimental evidence has been provided by fluorescence energy transfer measurements as well as X-ray and neutron scattering that human IgE adopts a bent structure which is speculated to contribute to the uniquely high affinity of IgE for Fc$\epsilon$RI (Kd~$10^{-10}$ M). Moreover, this bent structure is also postulated to be responsible for the equimolar complex between IgE and cell bound or soluble Fc$\epsilon$RI$\alpha$, although the IgE molecule would provide identical epitopes on the two C$\epsilon$3 domains for receptor binding. This monovalency is a functional necessity if receptor triggering in the absence of allergen is to be avoided (FIG. 1). Interactive sites, depending on their function, may already be exposed and therefore able to bind to cellular receptors. Alternatively, they may be hidden until the antibody binds to the antigen, whereupon the antibody may change in structure and subsequently expose other active sites which can then trigger a specific immune activity. Based on data obtained from circular dichroism spectra, a conformational rearrangement affecting C$\epsilon$3 upon receptor binding has been proposed as an explanation for the 1:1 stoichiometry of the Fc$\epsilon$/Fc$\epsilon$RI complex on the cellular surface.

For allergic (immunological) release of histamine within the organism from mast cells and basophils, an IgE molecule must lock onto or attach itself with its Fc portion to the cellular Fc receptor site, thus securing the IgE molecule to the mast cell or basophil. The Fab' portions of the cell-bound IgE molecules must be cross-linked by a particular compatible antigen (the allergen). When such an interaction occurs, the mast cell or basophil is automatically triggered to release histamine to the local environment, manifesting familiar allergic symptoms. Other biochemical events follow in a late phase reaction, resulting in de novo synthesis and release of cytokines and other mediators [Ravetch, J. V., and J. P. Kinet, *Ann. Rev. Immunol.* 9 (1991) 457–492].

Conventional approaches to allergy treatment have involved systemic therapy with anti-histamines or steroids or attempts to desensitize patients; these approaches are not adressed to the basic IgE-mast cell/basophil interaction. Other approaches have been concerned with the production of polypeptide chains capable of blocking the binding of the IgE antibody to the Fc receptors on the cell surfaces and displacing IgE from binding sites upon which IgE is already bound. Moreover, investigations have been carried out in order to define the nature of a putative "effector" site within the IgE Fc region, which was speculated to provide an immunological signal which triggers mast cells/basophils for mediator release.

Using recombinant IgE fragments as immunogens for the generation of a protective anti-IgE vaccine has also been tried and shown to be effective. The main argument against such a vaccine results from the fear that using large IgE fragments for immunization could initiate not only the production of inhibitory antibodies but also generate crosslinking and thereby anaphylactogenic antibodies in the patients (FIG. 2).

A strategy to overcome this problem would aim at the identification of the smallest IgE fragment possible, ideally consisting of the receptor binding site only, which is buried within the IgE/Fc$\epsilon$RI complex after binding and therefore no longer accessible for crosslinking by the vaccine-generated immune response. Attempts to reconstruct such a complex molecular entity seem unlikely to be successful in view of the spatial distances of the various C$\epsilon$3 regions involved in IgE/Fc$\epsilon$RI interaction.

SUMMARY OF THE INVENTION

It has now been found that the problems intrinsically linked to the "classical" vaccine approach are overcome by using BSW17 mimotopes for active immunization, either as chemically synthesized peptides coupled to appropriate carriers, or as recombinant fusion constructs (e.g. with ovalbumin, IgG, etc.).

BSW17 is a monoclonal antibody which recognizes a conformational epitope on Fcε with at least part of it residing within Cε3. The hybridoma cell-line producing monoclonal antibody BSW17 has been deposited on Dec. 19,/1996 with ECACC Salisbury, Wilthuv, SP4 OJE, United Kingdom under the provisions of the Budapest Treaty on the deposit of microorganisms, under deposit number 96121916. This antibody displays an interesting profile of biological activities, as summarized in FIG. 3. BSW17 or BSW17-like antibodies circulating within the vascular system protect from allergic reactions by a) inhibiting the triggering of mast cells and basophils through competitive inhibition of the IgE/IgERI interaction and b) lowering serum IgE levels through downregulation of IgE synthesis at the B cell level.

BSW17 "mimotope" peptides have now been identified by random peptide phage display library screening, i.e. peptides which mimic at least part of the complex conformational epitope on the IgE molecule. Chemically synthesized mimotope peptides coupled to an immunogenic carrier protein can be used e.g. as vaccines for the specific generation of antibodies in an allergic host which inhibit mast cell/basophil triggering by blocking IgE/FcεRIα binding and/or IgE synthesis. As mimotopes of an anti-IgE antibody they induce an immune response which results in the production of BSW17-like antibodies in the host. Since BSW17 has been shown to be non-anaphylactogenic, inhibitory to IgE/FcεRI binding and IgE synthesis on B cells, these antibodies raised against the BSW17 mimotope-based vaccines have analogous protective properties. The immune response is very specific since, in contrast to the "classical vaccine, approach", no IgE-derived protein fragments are present which could generate crosslinking antibodies in the immunized patients (FIG. 4).

The invention thus concerns immunogenic molecules comprising (a) at least one moiety of a BSW17 mimotope peptide and (b) a moiety capable of eliciting an immune response against that peptide, hereinafter briefly named "the immunogens of the invention".

Component (a) preferably consists of up to five, preferably one or two, especially one moiety of a BSW17 mimotope peptide. Component (b) preferably is a conventional immunogenic carrier as set out hereunder, especially BSA or KLH.

The BSW17 mimotope peptide in component (a) preferably is up to about 15 amino acids altogether, it is e.g. one of the sequences (A) to (Q) (Seq.id.no. 1 to no. 17) hereafter. However, it may appropriately include further components for hapten-carrier binding, e.g. to facilitate coupling to component (b) or further processing. Thus, when the BSW17 mimotope peptide is cyclic, the two ends can e.g. be held together by two additional cystein residues forming a disulfide bridge, or the ends can be chemically crosslinked, e.g. with lysine; or when the BSW17 mimotope peptide is linear, the carboxy terminal amino acid may conveniently be blocked by amidation, and/or the amino terminal amino acid may conveniently be blocked by acetylation. Further, the BSW17 mimotope peptide moieties in component (A), e.g. the preferred moieties (A) to (Q) hereafter, may be flanked in the immunogens of the invention by a few, preferably one or two, additional ancillary groups, such as acetyl, cysteine or lysine, and/or an additional coupling group, such as DC or BSS, e.g. as set out for the specific immunogens of the invention disclosed in Example 8 hereunder as conjugates (2) to (4), (6) to (11), (13) and (14).

The antibodies elicited by the immunogens of the invention, in contrast to the antibodies produced by hybridoma BSW17, will be endogenous and thus, in a patient, human; they may be used for prophylactic treatment.

They may be prepared by appropriately coupling components (a) and (b) as defined above.

DETAILED EXPLANATION

The immunogens of the invention are e.g. in the form of a polymeric peptide or a recombinant fusion protein, whereby a monomeric component of the polymeric peptide, or one partner of the fusion protein, constitutes a moiety of a BSW17 mimotope peptide (a) and the remainder of the polymeric peptide or fusion protein constitutes the immune response-eliciting moiety (b).

They especially are in the form of a conjugate of at least one BSW17 mimotope peptide moiety (a) and an immunogenic carrier moiety (b).

Preferred BSW17 mimotope peptide moieties, i.e. component (a), of the immunogens of the invention essentially consist of or contain an amino acid sequence selected from

| | | |
|---|---|---|
| Ile-Asn-His-Arg-Gly-Tyr-Trp-Val | (A) | (Seq.id.no. 1), |
| Arg-Asn-His-Arg-Gly-Tyr-Trp-Val | (B) | (Seq.id.no. 2), |
| Arg-Ser-Arg-Ser-Gly-Gly-Tyr-Trp-Leu-Trp | (C) | (Seq.id.no. 3), |
| Val-Asn-Leu-Thr-Trp-Ser-Arg-Ala-Ser-Gly | (D) | (Seq.id.no. 4), |
| Val-Asn-Leu-Pro-Trp-Ser-Arg-Ala-Ser-Gly | (E) | (Seq.id.no. 5), |
| Val-Asn-Leu-Thr-Trp-Ser-Phe-Gly-Leu-Glu | (F) | (Seq.id.no. 6), |
| Val-Asn-Leu-Pro-Trp-Ser-Phe-Gly-Leu-Glu | (G) | (Seq.id.no. 7), |
| Val-Asn-Arg-Pro-Trp-Ser-Phe-Gly-Leu-Glu | (H) | (Seq.id.no. 8), |
| Val-Lys-Leu-Pro-Trp-Arg-Phe-Tyr-Gln-Val | (I) | (Seq.id.no. 9), |
| Val-Trp-Thr-Ala-Cys-Gly-Tyr-Gly-Arg-Met | (J) | (Seq.id.no. 10), |
| Gly-Thr-Val-Ser-Thr-Leu-Ser | (K) | (Seq.id.no. 11), |
| Leu-Leu-Asp-Ser-Arg-Tyr-Trp | (L) | (Seq.id.no. 12), |
| Gln-Pro-Ala-His-Ser-Leu-Gly | (M) | (Seq.id.no. 13), |
| Leu-Trp-Gly-Met-Gln-Gly-Arg | (N) | (Seq.id.no. 14), |
| Leu-Thr-Leu-Ser-His-Pro-His-Trp-Val-Leu-Asn-His-Phe-Val-Ser | (O) | (Seq.id.no. 15), |
| Ser-Met-Gly-Pro-Asp-Gln-Thr-Leu-Arg | (P) | (Seq.id.no. 16), or |
| Val-Asn-Leu-Thr-Trp-Ser | (Q) | (Seq.id.no. 17). |

More preferred are (A), (D) and (G) above, especially (A) and (D).

The invention also concerns pharmaceutical compositions, especially vaccines, comprising immunogen molecules as defined above and an adjuvant.

It also concerns ligands, i.e. antibodies or fragments derived therefrom directed against BSW17 mimotope peptides used in "passive immunization" (see below), whereby the antibody or antibody fragments also recognize the natural epitope for BSW17 on human IgE; namely, it concerns ligands comprising an antibody domain specific for a moiety of a BSW17 mimotope peptide as defined above, whereby the antibody domain is reactive also with the sequence of amino acids on the heavy chain of IgE which comprises the natural epitope recognized by BSW17. Such ligands can be generated in mammals as polyclonal or monoclonal antibodies; they preferably are in the form of monoclonal antibodies, preferably in the form of an Fab' fragment or an $F(ab')_2$ fragment thereof.

It further concerns a process for the preparation of an immunogen of the invention, comprising covalently coupling a) at least one moiety of a BSW17 mimotope peptide with b) a moiety capable of eliciting an immune response against that peptide.

It also concerns immunogenic molecules as defined above, for use as a pharmaceutical, e.g. in the treatment of IgE-mediated diseases such as allergy and atopic dermatitis.

It further concerns the use of immunogenic molecules as defined above in the preparation of pharmaceutical compositions, especially vaccines, against IgE-mediated diseases, in particular allergy and atopic dermatitis.

It further concerns a method of prophylactic or curative immunization against IgE-mediated diseases such as allergies and atopic dermatitis comprising the administration of a therapeutically effective amount of immunogenic molecules as defined above to a patient in need of such treatment.

The immunogens of the invention, while being substantially incapable of mediating non-cytolytic histamine release, are capable of eliciting antibodies with strong serological cross-reactivity with the target amino acid sequences of the Fc region of IgE. They are thus useful in, or as, vaccines.

The initial dose of immunogen (e.g. from about 0.2 mg to about 5 mg, especially about 1 mg) is for example administered intramuscularly, followed by repeat (booster) doses of the same 14 to 28 days later. Doses will of course depend to some extent on the age, weight and general health of the patient. Immunization may be "active" or "passive".

In "active" immunization the patient receives immunogen of the invention and thereby an anti-hIgE response is actively induced by the patient's immune system.

"Passive" immunization is achieved by administering anti-BSW17 mimotope antibodies, either polyclonal or monoclonal, to a patient suffering from IgE-mediated disease, preferably by injection.

Polyclonal anti-BSW17 mimotope antibodies can be prepared by administering immunogen of the invention, preferably using an adjuvant, to a non-human mammal and collecting the resultant antiserum. Improved titres can be obtained by repeated injections over a period of time. There is no particular limitation to the species of mammals which may be used for eliciting antibodies; it is generally preferred to use rabbits or guinea pigs, but horses, cats, dogs, goats, pigs, rats, cows, sheep, etc., can also be used. In the production of antibodies, a definite amount of immunogen of the invention is e.g. diluted with physiological saline solution to a suitable concentration and the resulting diluted solution is mixed with complete Freund's adjuvant to prepare a suspension. The suspension is administered to mammals, e.g. intraperitoneally, e.g. to a rabbit, using from about 50 $\mu$g to about 2500 $\mu$g immunogen of the invention per administration. The suspension is preferably administered about every two weeks over a period of up to about 2–3 months, preferably about 1 month, to effect immunization. Antibody is recovered by collecting blood from the immunized animal after the passage of 1 to 2 weeks subsequently to the last administration, centrifuging the blood and isolating serum from the blood.

Monoclonal anti-BSW17 mimotope antibodies may e.g. be human or murine. Preferably, the patient will be treated with an Fab' fragment preparation from murine monoclonal antibody or a chimeric human-mouse antibody (comprising human Fc region and mouse Fab' region) so as to minimize any adverse reaction to the foreign animal immunoglobulin. Murine monoclonal antibodies may be prepared by the method of Köhler and Milstein (Köhler, G. and Milstein, C., *Nature* 256 [1975] 495), e.g. by fusion of spleen cells of hyperimmnunized mice with an appropriate mouse myeloma cell line. Numerous methods may be utilized to raise human monoclonal antibodies, including production by:

(1) Epstein-Barr virus (EBV)—transformed B-cells;

(2) cell line for B lymphocyte hybridization;

(3) human-murine hybridomas;

(4) human-human hybridomas;

(5 ) human x human-mouse heterohybridomas; and (6) repertoire cloning (phage display).

Human x human-mouse heterohybridomas are the most preferred, and involve combining favourable characteristics of both human and murine parental cell types. Human-mouse heterohybridoma cell lines have been rendered suitable for B cell fusion (Teng, N. N. M. et al., *Proc. Natl. Acad. Sci. USA* 80 [1983] 7308).

When used for immunization, antibody can be introduced into the host most conveniently by intramuscular injection. Any conventional liquid or solid vehicle may be employed which is acceptable to the host and does not have adverse side effects on the host nor detrimental effects on the vaccine. Phosphate-buffered saline (PBS), at a physiological pH, e.g. about pH 6.8 to 7.2, preferably about pH 7.0, may be used as a vehicle, alone or with a suitable adjuvant, such as an aluminium hydroxide-based adjuvant. The concentration of immunogenic antigen may vary from about 50 $\mu$g to about 500 $\mu$g, preferably from about 200 $\mu$g to about 300 $\mu$g per injection, in a volume of solvent generally of from about 0.25 ml to about 1 ml, preferably about 0.5 ml. Multiple injections will be required after the initial injection and may be given e.g. at annual intervals.

As regards "active" immunization, this is preferred for human use, but other mammalian species may be treated similarly, using analogous mimotopes corresponding to the IgE of these specie, as e.g. in the dog. The term "immunogenic carrier" herein includes those materials which have the property of independently eliciting an immunogenic response in a host animal and which can be covalently coupled to polypeptide either directly via formation of peptide or ester bonds between free carboxyl, amino or hydroxyl groups in the polypeptide and corresponding groups on the immunogenic carrier material, or alternatively by bonding through a conventional bifunctional linking group, or as a fusion protein.

Examples of such carriers include: albumins, such as BSA; globulins; thyroglobulins; hemoglobins; hemocyanins (particularly Keyhole Limpet Hemocyanin [KLH]); proteins extracted from ascaris, e.g. ascaris extracts such as those described in *J. Immun.* 111 [1973] 260–268, *J. Immun.* 122 [1979] 302–308, *J. Immun.* 98 [1967] 893–900, a *Am. J. Physiol.* 199 [1960] 575–578 or purified products thereof; polylysine; polyglutamic acid; lysine-glutamic acid copolymers; copolymers containing lysine or ornithine; etc. Recently, vaccines have been produced using diphteria toxoid or tetanus toxoid as immunogenic carrier material (Lepow M. L. et al., *J. of Infectious Diseases* 150 [1984] 402–406; Coen Beuvery, E. et al., *Infection and Immunity* 40 [1983] 39–45) and these toxoid materials can also be used in the present invention. The purified protein derivative of tuberculin (PPD) is particularly preferred for utilization in the "active" immunization scheme since (I) it does not induce a T-cell response itself (i.e. it is in effect a "T-cell hapten"), and yet behaves as a fully processed antigen and is recognized by T-cells as such; (2) it is known to be one of the most powerful hapten "carriers" in the linked recognition mode; and (3) it can be used in humans without further testing.

As hapten-carrier binding agents, those conventionally employed in the preparation of antigens can be employed, e.g. those set out above, or in the Examples hereunder.

The process of the invention for covalently coupling component (a) to moiety (b) can be effected in known manner. Thus, for example, for direct covalent coupling it is preferred to utilize bis-N-succinimidyl derivatives, more preferably bis(sulfosuccinimidyl)suberate (BSS) as coupling agent. Glutaraldehyde or carbodiimide, more preferably dicyclohexyl-carbodiimide (DC) or 1-ethyl-3-(3-dimethylaminopropyl) carbodiimide may also be used for covalent coupling of peptide (a) to immunogenic carrier material (b).

The amounts of hapten and hapten-carrier binding agent [i.e. component (a)] and carrier [i.e. component (b)] can be readily ascertained in conventional manner. It is preferred that the carrier be employed in an amount of about 1 to about 6 times, preferably about 1 to about 5 times the weight of the hapten, and the hapten-carrier binding agent be employed in an amount of about 5 to about 10 times the molar equivalent of the hapten. After reaction, the carrier is bound to the hapten via the hapten-carrier binding agent to obtain the desired antigen composed of a peptide-carrier complex. The resultant immunogen of the invention can be readily isolated in conventional manner, e.g. by dialysis, gel filtration, fractionation precipitation, etc.

The preparation of the starting materials may be effected in conventional manner. Appropriate peptides for use as component (a) may e.g. be identified by screening of random peptide phage display libraries, and readily synthesized e.g. by conventional solid phase procedures, e.g., for cyclic peptides, by the solid phase procedure employing the well-known "F-moc" procedure, or may alternatively be identified using a peptidomimetic strategy by screening of randomly synthesized peptides.

EXPLANATION OF THE FIGURES

The patent or application file contains at least one drawing executed in color. Copies of this patent or patent application publication with color drawing(s) will be provided by the Office upon request and payment of the necessary fee.

FIG. 4: BSW17 mimotope-based immunotherapy

FIG. 7: Binding of a chemically synthesized BSW17 mimotope peptide to BSW17

FIG. 8a: Recognition of cyclic BSW17 mimotope GEFCINHRGYWVCGDPA-KLH SEQ ID NO.33 (BSS) conjugate (SDS 236) and Fcε (500–509)-KLH (BSS) conjugate (SDS 237) by BSW17

FIG. 8b: Recognition of various BSW17 mimotope conjugates by BSW17

FIG. 9a: Specific recognition of BSW17 mimotope conjugates [BSA (DC)] and Fcε (500–509) conjugate [KLH (glutaraldehyde)] by BSW17

FIG. 9b: Specific recognition of BSW17 mimotope conjugates [KLH (DC); Lys] by BSW17

FIG. 10a: Anti-human IgE immune response induced in rabbits after immunization with BSW17 mimotope conjugates (1)

FIG. 10b: Anti-human IgE immune response induced in rabbits after immunization with BSW17 mimotope conjugates (2)

FIG. 11a: Serum titers of anti BSW17 mimotope antibodies generated in rabbits by immunization of rabbits with BSW17 mimotope-KLH conjugate SDS 213

FIG. 11b: Serum liters of anti BSW17 mimotope antibodies generated in rabbits by immunization of rabbits with BSW17 mimotope-KLH conjugate SDS 214

FIG. 13: Competition of anti BSW17 mimotope serum with BSW17 for IgE binding

Figure 1:
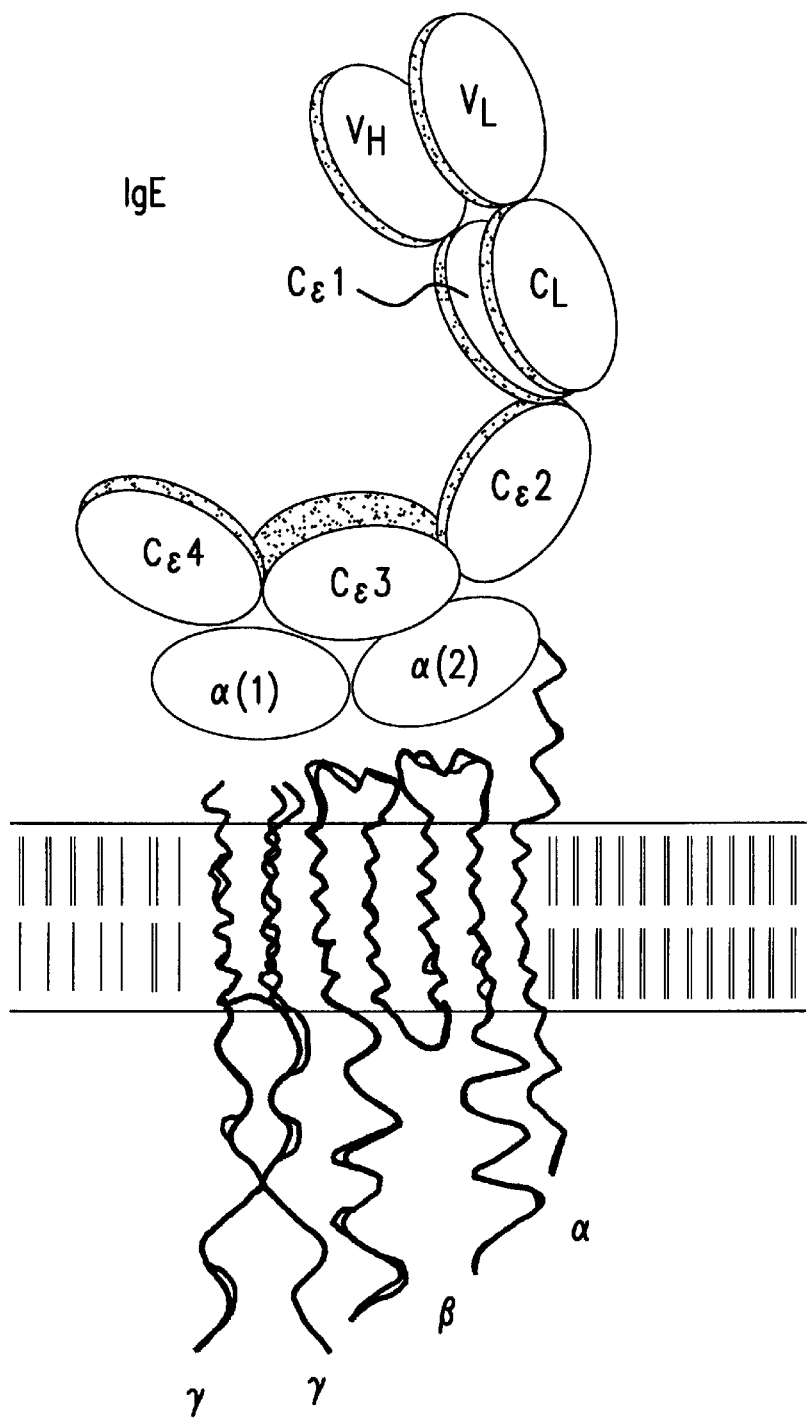
FIG. 1: Interaction between IgE and its high affinity receptor IgERI
Figure 2:
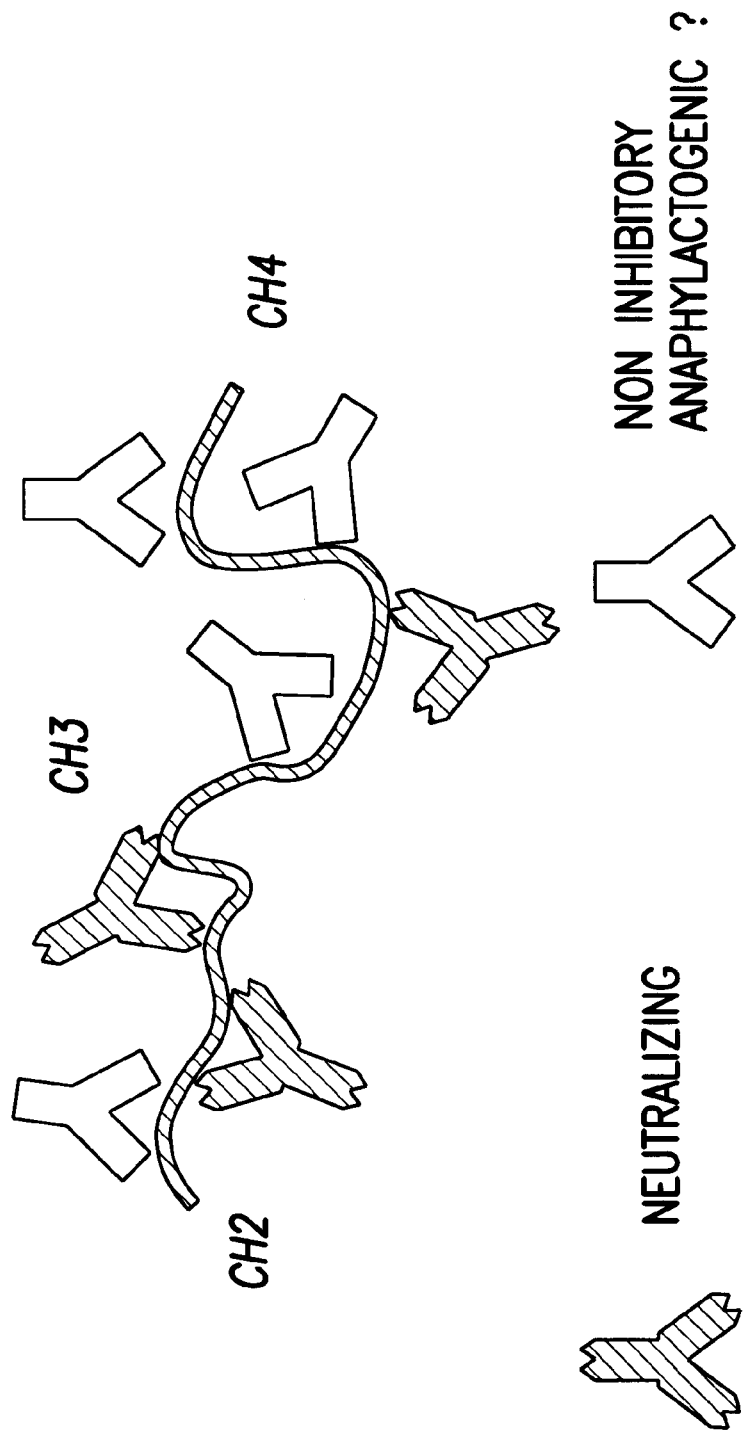
FIG. 2: "Classical" anti-IgE vaccine approach
Figure 3:
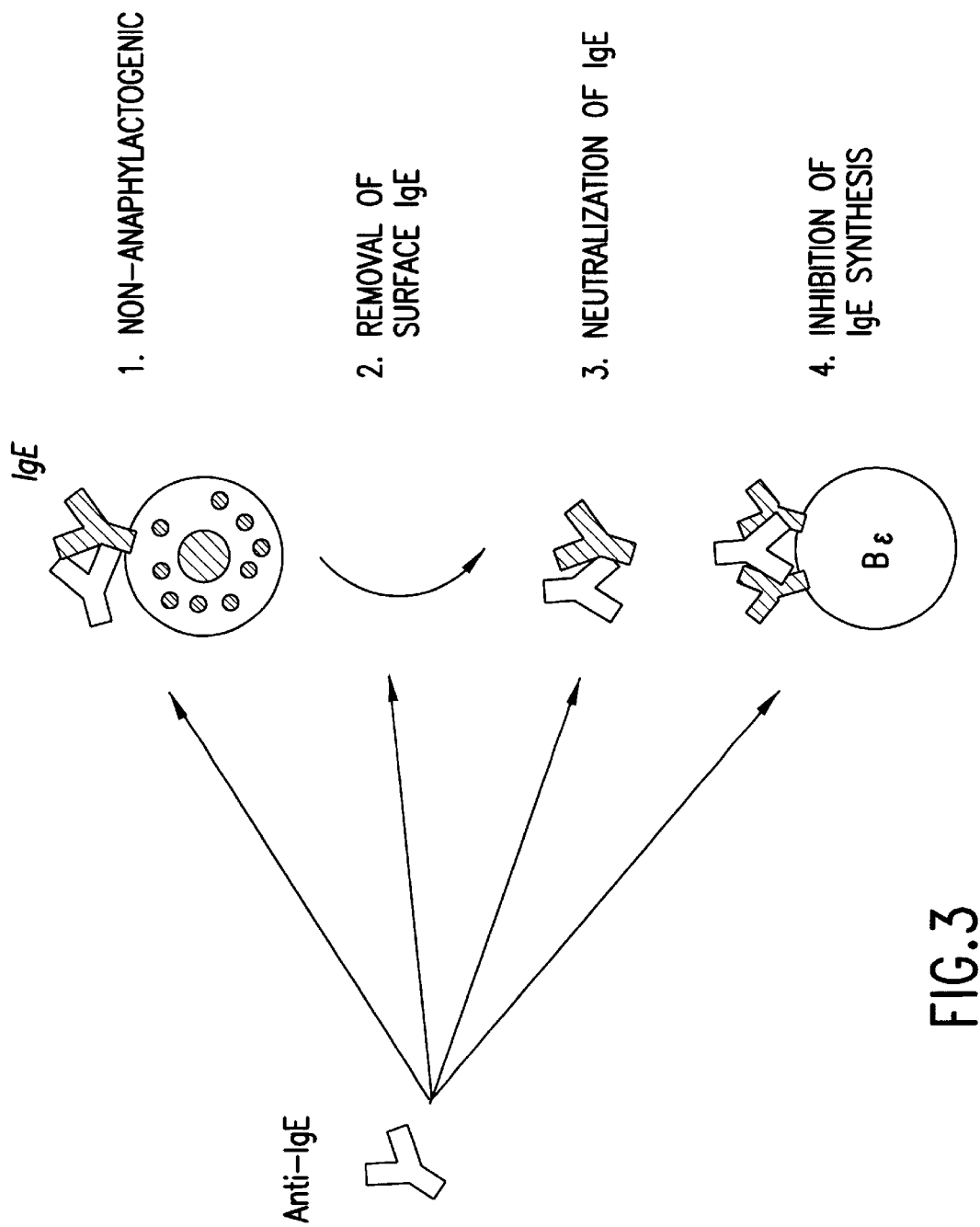
FIG. 3: Biological activity profile of BSW17

R2/0, R4/0: pre immune sera of rabbits R2 and R4 prior to BSW17 mimotope vaccination;

R2/SDS214, R4/SDS213: sera of rabbits R2 and R4 65 days after primary immunization;

antiSDS213, antiSDS214: affinity-purified anti-BSW17 mimotope antibodies;

R2/0 PC, R4/0 PC: positive triggering control (PC) in the presence of rabbit serum.

SAMPLE CONCENTRATIONS

A =0.1 μg anti-BSW17 mimotope antibodies (or equivalents in complete rabbit sera) per ml B =1.0 μg anti-BSW17 mimotope antibodies (or equivalents in complete rabbit sera) per ml C =5.0 μg anti-BSW17 mimotope antibodies (or equivalents in complete rabbit sera) per ml.

| Abbreviations: | |
|---|---|
| Ac | acetyl |
| AMS | ammonium sulphate |
| BSA | bovine serum albumin |
| BSS | bis(sulfosuccinimidyl)suberate |
| BSW17 | an IgG monoclonal antibody directed against the CH₃ epitope of native IgE (J.Knutti-Müller et al., Allergy 41 [1986] 457–465; S.Miescher et al., Int.Arch.Allergy Immunol. 105 [1994] 75) |
| BSW 17 mimotope peptide | a peptide mimicking the natural epitope on human IgE recognized by the monoclonal anti-human IgE antibody BSW17 |
| cfu | colony-forming units |
| DC | dihexylcarbodiimide |
| EBV | Epstein-Barr virus |
| ELISA | enzyme-linked immunosorbent assay |
| FcεRI | high-affinity receptor 1 for the constant region of IgE |
| FCS | fetal calf serum |
| gam | goat anti-mouse |
| gar | goat anti-rabbit |
| h | human |
| HEPES | N-2-hydroxyethylpiperazine-N'-2-ethanesulfonic acid |
| HRP | horse raddish peroxidase (= POX) |
| HSA | human serum albumin |
| IgE | immunoglobulin E |
| IPTG | isopropyl-β-D-thiogalactoside |
| KLH | keyhole limpet hemocyanin |
| Le27 | a monoclonal anti-human IgE antibody (Allergy [1986], supra; Int.Arch.Allergy Immunol. [1994] supra) |
| LB-plates | Luria-Bertani medium plates |
| mimotope peptide | a peptide which mimicks at least part of the conformational epitope of an antibody molecule |
| PBS | phosphate-buffered saline |
| PEG | polyethyleneglycol |
| POX | horse radish peroxidase (= HRP) |
| PPD | purified protein derivative of tuberculin |
| rh IL-3 | recombinant human interleukin-3 |
| RIA plates | radioimmunoassay plates |
| RPMI1640 | standard cell culture medium (Sigma, St. Louis, USA) |
| SB-medium | Sodium - Bacto medium (Pharmacia, Uppsala, Sweden) |
| sLt | soluble leukotriene |
| TBS | Tris-buffered saline |
| VCS | VCS M13 helper phage (Stratagene, USA). |

EXAMPLES

In the following Examples, which illustrate the invention but in no way limit its scope, references to temperature are in degrees Celsius.

Example 1
Anti-allergic Potential of the Anti-hIgE Monoclonal Antibody BSW17

As a model for testing the anti-allergic capacity of BSW17 and BSW17-like antibodies generated in human patients by active immunization with BSW17 mimotope peptides, the effect of BSW17 on the histamine release of human basophil-like cells, obtained from bone marrow cells cultured with rhIL-3, is shown.

Mononuclear cells are prepared from bone marrow from patients requiring femur bone head replacement FICOLL-HYPAQUE® density sedimentation (1.077 g/ml; 400 g). $5 \times 10^5$ cells/ml are cultured in RPM1640 medium containing 15% FCS and 2 ng/ml human rhIL-3. After 6 days of culture at 37° in 5% $CO_2$, an equal volume of medium containing rhIL-3 is added. On day 12, cells are harvested and used for passive sensitization and histamine release assay. Approximately $5 \times 10^5$ cultured bone marrow cells are incubated in HA buffer (20 MM HEPES; pH=7.4; 0.3 mg/ml HSA) with 500 ng/ml of human IgE in the presence or absence of a 50-fold excess of monoclonal anti-IgE: antibody in a total volume of 1 ml. After incubation for 2 hours at 37°, cell supernatants are used to measure histamine during passive sensitization. Cell pellets are used to trigger histamine release. To determine the extent of direct histamine release, the passively sensitized bone marrow cells are resuspended in 0.3 ml of HCM buffer (HA buffer containing 0.6 M $CaCl_2$ and 1 mM $MgCl_2$ and incubated with 0.1 µg/ml of the anaphylactogenic monoclonal anti-IgE antibody Le27. The amount of histamine in the supernatant and in the cellular sediment is measured in a Technicon Autoanalyzer II (Technicon, Tarrytown, N.Y., USA). Percentage of histamine release is calculated [according to the formula: histamine release (%)=histamine in the supernatant divided by histamine in the supernatant+histamine in the cell pellet, multiplied by 100]. Percentage of histamine release during passive 'sensitization is calculated [according to the formula: histamine release (%)=histamine in the supernatant (after passive sensitization) divided by histamine in the supernatant (after triggering)+histamine in the supernatant (after sensitization)+histamine in the cell pellet, multiplied by 100]. Anti-IgE antibody-specific histamine release is calculated [according to the formula: specific histamine release (%)=% total histamine release, minus % spontaneous histamine release].

The results of three independent experiments are summarized in Table 1:

TABLE 1

Effect of anti-IgE antibodies on histamine release of sensitized bone marrow cells

| | Specific histamine release (%)** | | | | | |
|---|---|---|---|---|---|---|
| | Experiment 1 | | Experiment 2 | | Experiment 3 | |
| Sensitized with* | A | B | A | B | A | B |
| IgE(control) | 3.0 | 10.3 | 4.3 | 11.0 | 1.5 | 36.5 |
| +BSW17 | 3.6 | 3.1 | 3.0 | 1.5 | 4.4 | 0.9 |
| +Le27 | 11.0 | 2.7 | 8.7 | 1.7 | 15.7 | 3.8 |

*Human bone marrow cells cultured with rhIL-3 (2 ng/ml ) are passively sensitized with IgE (0.5 µg/ml ) or with IgE and anti-IgE antibodies ( 0.25 µg/ml )
**A: Histamine release during sensitization
B: Histamine release after triggering with the monoclonal anti-IgE antibody Le27 (0.1 µg/ml).

The data in Table 1 clearly shows that bone marrow cells incubated with IgE and BSW17 do not release histamine during sensitization but inhibit subsequent triggering with Le27. Bone marrow cells incubated with IgE and Le27 are triggered already during passive sensitization to an extent that no more histamine can be released during the second incubation with this anaphylactogenic monoclonal antibody. Bone marrow cells passively sensitized in the absence of either monoclonal anti-IgE antibody, however, effectively release histamine after subsequent triggering with Le27.

It can be concluded that a) BSW17 by itself is non-anaphylactogenic and b) BSW17 protects human basophils from histamine release induced by triggering agents. Therefore, the generation of BSW17-like antibodies in allergic patients by active immunization with BSW17 mimotope peptides can be expected to protect immunized hosts from the development of allergic reactions.

Example 2
Random Peptide Phage Display Library Screening and Selection of Positive Clones Bacteriophage particles specifically recognized by BSW17 are identified by biopanning of phage libraries displaying linear or circular random peptides from 6 to 15 amino acid residues in length fused to phage peptides pIII and pVIII, respectively. For amplification of phage libraries, 2 ml of a liquid culture of E. coli XL-I blue grown in SB medium to $OD_{600}=1.0$ are incubated with $10^{10}$ phages for 15 minutes at room temperature. 10 ml of SB medium containing 10 mg/ml of tetracycline and 20 μg/ml of carbenicillin are added and 10 μl, 1 μl and 0.1 μl, respectively, are plated on LB plates containing 100 μg/ml of carbenicillin. The culture is incubated at 37° with vigorous shaking for one hour, then 100 ml of SB containing 10 μg/ml of tetracycline and 50 μg/ml of carbenicillin are added and incubation is continued for one hour. $10^{12}$ cfu of VCS M13 helper phage are added. After 2 hours with vigorous shaking at 37°. kanamycin is added to a final concentration of 70 μg/ml and incubation continued overnight. After centrifugation at 4000 g and 4° for 20 minutes, supernatants are mixed with 38 ml of an ice-cold sterile filtered solution of 12% NaCl and 16% PEG 8000, cooled on ice for 30 minutes and centrifuged for 30 minutes at 10000 g at 4°. The phage pellet is solubilized in 2 ml of TBS containing 1.5% casein and stored at 4°. For biopanning, COSTAR® RIA plates (Costar 3690) are coated over-night at 4° with 20 μg/ml of BSW17 in 0.1 M carbonate buffer, pH 9.6, and thereafter blocked with TBS containing 1.5% casein. $2\times10^{11}$ cfu of phages are added and incubated at 37° for 2 hours, then washed ten times with PBS/0.1% Tween 20. The wells are rinsed with water and the bound phages eluted with a total of 200 μl of 0.1 M HCl, pH 2.2 for 10 minutes. Eluted phages are neutralized with 2 M Tris base and amplified as described above.

For the selection of positive clones 50 μl of a E. coli XL-I blue liquid culture grown in SB-medium to $OD_{600}=1.0$ are incubated with 1 μl of a $10^{-8}$ dilution of amplified phages after the 3rd round of panning for 15 minutes at room temperature, then plated on LB plates containing 100 μg/ml of carbenicillin and grown overnight. Colonies are randomly picked and plated on LB plates containing 100 μg/ml of carbenicillin. After 4 hours at 37°, nitrocellulose filters soaked with 10 mM of IPTG are put on top and incubation continued overnight at 32°. Filters are removed and incubated at 37° for 30 minutes in a $CHCl_3$-atmosphere. Bacterial debris are removed by incubating the filters in 50 mM Tris, pH 8, 150 mM NaCl, 5 mM $MgCl_2$, 3% BSA, 100 U DNAaseI and 40 mg lysozyme per 100 ml for 1 hour, blocked in TBS containing 1.5% casein and incubated overnight with BSW17-POX (BSW17 coupled to POX) in TBS containing 1.5% casein. Filters are washed with TBS, TBS/ 0.5% Tween 20 and then TBS for 10 minutes each. For staining the strips are incubated in 600 μg of 4-chloro-1-naphthol per ml and 0.042% of hydrogen peroxide in TBS.

Example 3

Characterization of Phage Particles Displaying Peptides Which Mimick the Natural BSW17 Epitope (BSW17 Mimotope Peptides)

Various phage particles displaying circular peptides consisting of seven, eight or nine amino acids and linear peptides consisting of ten and fifteen amino acid residues, respectively, have been found to bind to BSW17. The nucleotide sequence of the DNA encoding these peptides was determined. According to their homology among each other as well as to homologous regions within Fcε, 3 groups of phages displaying peptides recognized by BSW17 could be deduced from the DNA sequence. An overview is shown in Table 2:

TABLE 2

Peptide sequences displayed by BSW17 mimotope phages
GROUP A:

| | | | | | | | | | | | | |
|---|---|---|---|---|---|---|---|---|---|---|---|---|
| | + | + | + | p | p | p | o | o | o | | | |
| Cys | Arg | Arg | His | Asn | Tyr | Gly | Phe | Trp | Val | Cys | n = 7 | ++ |
| | o | p | + | + | | p | p | o | o | | | |
| Cys | Ile | Asn | His | Arg | | Gly | Tyr | Trp | Val | Cys | n = 3 | +++ |
| | p | + | o | + | p | p | p | o | o | | | |
| Cys | Thr | Arg | Leu | His | Thr | Gly | Tyr | Trp | Val | Cys | n = 2 | + |
| | p | o | p | o | o | p | p | o | o | | | |
| Cys | Thr | Leu | Ser | Val | Phe | Gly | Tyr | Trp | Val | Cys | n = 1 | +/− |

+ = positively charged
p = uncharged polar
o = non polar
n = number of clones displaying the corresponding sequence
+(++), +/− = intensity of recognition by BSW 17
(i.e. Seq.id.no. 18, no. 19, no. 20, and No. 21, respectively)
The second peptide of group A above (Seq.id.no. 19) is peptide (A) (Seq.id.no. 1) with two additional Cys for circularization. The other three peptides, Seq.id.no. 18, Seq.id.no. 20, and Seq.id.no. 21, respectively, are further similarly prepared peptides.

GROUP B:

| | | | | | | | | | |
|---|---|---|---|---|---|---|---|---|---|
| Val | Asn | Leu | Pro | Trp | Ser | Phe | Gly | Leu | Glu |
| Val | Asn | Arg | Pro | Trp | Ser | Phe | Gly | Leu | Glu |
| Val | Lys | Leu | Pro | Trp | Arg | Phe | Tyr | Gln | Val |

The three peptides of group B above are peptides (G) (Seq.id.no. 7), (H) (Seq.ld.no. 8) and (I) (Seq.id.no. 9), respectively.

GROUP C:

| | | | | | | | | | | | | | | |
|---|---|---|---|---|---|---|---|---|---|---|---|---|---|---|
| Leu | Thr | Leu | Ser | His | Pro | His | Trp | Val | Leu | Asn | His | Phe | Val | Ser |
| Val | Trp | Thr | Ala | Cys | Gly | Tyr | Gly | Arg | Met | | | | | |

-continued

GROUP C:

| Cys | Ser | Met | Gly | Pro | Asp | Gln | Thr | Leu | Arg | Cys |
| Cys | Leu | Leu | Asp | Ser | Arg | Tyr | Trp | Cys | | |
| Cys | Gln | Pro | Ala | His | Ser | Leu | Gly | Cys | | |
| Cys | Leu | Trp | Gly | Met | Gln | Gly | Arg | Cys | | |
| Cys | Gly | Thr | Val | Ser | Thr | Leu | Ser | Cys | | |

The 7 peptides of group C above are, respectively, peptide (O) (Seq.id.no. 15), peptide (J) (Seq.id.no. 10), peptide (P) with two additional Cys (Seq.id.no. 22), peptide (L) with two additional Cys (Seq.id.no. 23), peptide (M) with two additional Cys (Seq.id.no. 24), peptide (N) with two additional Cys (Seq.id.no. 25), and peptide (K) with two additional Cys (Seq.id.no. 26). The peptides of group C containing flanking Cys are strong BSW17 binders. The whole group C does not display sequence homology with Fcε; the peptides are genuine mimotopes mimicking the BSW17 epitope only structurally.

As can be seen from Table 2, the carboxy-terminal parts of the peptides from group A are highly conserved and the amino-terminal parts, though more degenerated, contain positively-charged, polar amino acids. This charge distribution seems to be essential for BSW17 recognition, since one clone which differs in the amino-terminus from this feature proves to only very weakly bind to BSW17. No consecutive stretch of amino acids with significant sequence homology can be found in Fcε. Alignment by pattern similarity, however, allows allocation of these peptides to a stretch of amino acids ranging from position 500 to 508 within the Cε4 domain. The decapeptide Fcε 500–509 has been postulated by Stanworth et al. [*Lancet* 336 (1990)1279] to be involved in mast cell triggering by receptor-bound IgE.

Peptides belonging to group B also are highly homologous among each other. Furthermore, their amino-terminal part is almost identical with amino acid positions 370–375 of Fcε. This sequence is part of Cε3 and contains or is adjacent to a region which has been shown to be involved in binding of IgE to its high affinity receptor. This finding explains the inhibiton of the IgE/IgERI interaction by BSW17.

It can be concluded that the complex conformational epitope recognized by BSW17 contains conformational structures represented by amino acid stretches 500–508 (within Cε4) and 370–375 (within Cε3) of the IgE molecule (numbering according to E. A. Padlan and D. R. Davies, *Molecul.Immunol.* 23 (1986) 1063). Antibodies generated in an individual by immunization with mimotopes from groups A and B above coupled to an immunogenic carrier molecule will thus protect from allergic reactions by blocking the binding of IgE to its high affinity receptor and/or triggering the degranulation of target cells.

Peptides summarized in group C of the table exhibit no significant homologies among each other nor with Fcε. Therefore, they represent "genuine mimotopes" mimicking the three dimensional structure recognized by BSW17. Using these mimotopes as immunogens thus will also result in the generation of anti-allergic, BSW17-like antibodies in the immunized host.

The generation of a BSW17-like immune response specifically directed against the BSW17 epitope on human IgE is shown for selected mimotopes in the following Examples 4 to 6:

Example 4
Bacteriophages Displaying BSW17 Mimotope Peptides are Specifically Recognized by BSW17

Figure 5:
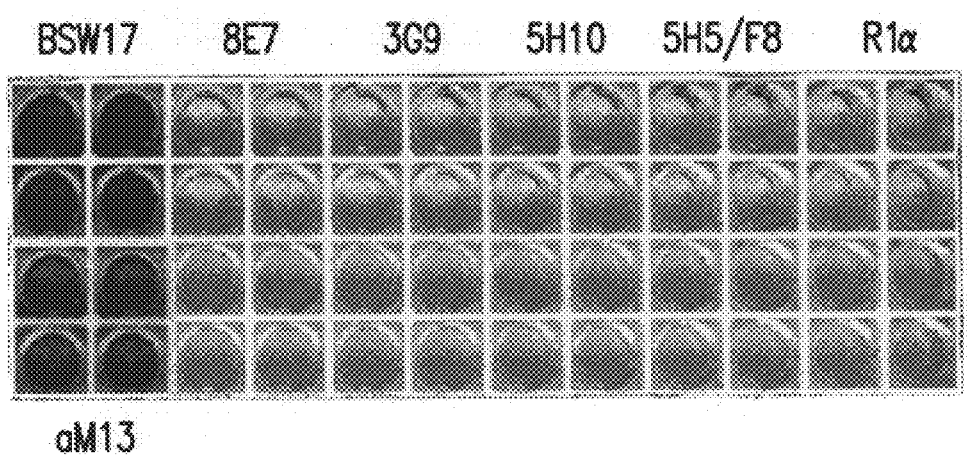
FIG. 5: Phage-displayed BSW17 mimotopes specifically recognize BSW17

Binding of mimotope peptides displayed by phage particles (group A of Table 2: first clone=clone 1 in FIG. 5=Cys-Arg-Arg-His-Asn-Tyr-Gly-Phe-Trp-Val-Cys=Seq.id.no. 18; second clone=clone 18 in FIG. 5=Cys-Ile-Asn-His-Arg-Gly-Tyr-Trp-Val-Cys=Seq.id.no. 19) to the antigen-specific hypervariable regions of BSW17 is demonstrated by ELISA. 10 μg of BSW17 and various monoclonal antibodies are coated to the wells of COSTAR® plates following standard ELISA procedures. After blocking with BSA, the wells are incubated with 100 μl of standard ELISA incubation buffer containing bacteriophage particles obtained from phage-infected bacterial culture supernatants with a phage titer of $10^9$ cfu/ml. After washing, the plates are incubated with 5 μg of horseradish peroxidase (HRP)-coupled anti-M13 antiserum (Pharmacia, Uppsala, Sweden) in incubation buffer. All incubations are carried out at room temperature for 1 hour. After final washing, phage particles bound to the coated antibodies are visualized via the bound HRP-anti M13 serum by chromogenic substrate development following standard ELISA procedure. FIG. 5 shows that mimotope phages very specifically bind to BSW17 and to no other antibodies, such as 8E7, 3G9 and 5H10 which are also monoclonal anti-Cε3 antibodies and which have been generated by using recombinant Cε3 as immunogen, nor to 5H5/F8 which represents another monoclonal antibody which is directed against the extracellular portion of human FcεRIα. As negative non-antibody control, recombinant FcεRI α-chain and as positive control, wells coated with polyclonal anti-M13 antiserum are included.

Example 5
Bacteriophages Displaying BSW17 Mimotope Peptides Competitively Inhibit the Binding of BSW17 to IGE The specificity of the mimotope-BSW17 interaction is further demonstrated by showing that the attachment of mimotope-displaying phage particles interferes with the BSW17/IgE binding. Bacterial cells are grown in SB containing 10 μg/ml of tetracycline and 50 μg/ml of carbenicillin to $OD_{600}$=0.4, then VCS M13 helper phage is added and incubation continued for 2 hours at 37°. Then kanamycin is added to a final concentration of 70 μg/ml and incubation continued overnight. Phage particles are precipitated with polyethyleneglycol. Soft RIA plates are coated with 20 μg/ml of BSW17 in 0.1 M carbonate buffer pH 9.6 and then blocked with TBS containing 1.5% casein. Human IgE is $^{125}$I-labelled by the chloramine-T method and 100000 cpm per well are used for binding to BSW17 coated to the RIA plates in the presence of increasing concentrations of non-labelled IgE (standard curve) or phage particles, respectively. All experiments are performed at room temperature and plates are washed 3 times with 0.9% NaCl+0.05% Tween 20, cut in pieces and each well was measured in a γ-counter for 1 minute.

Figure 6:
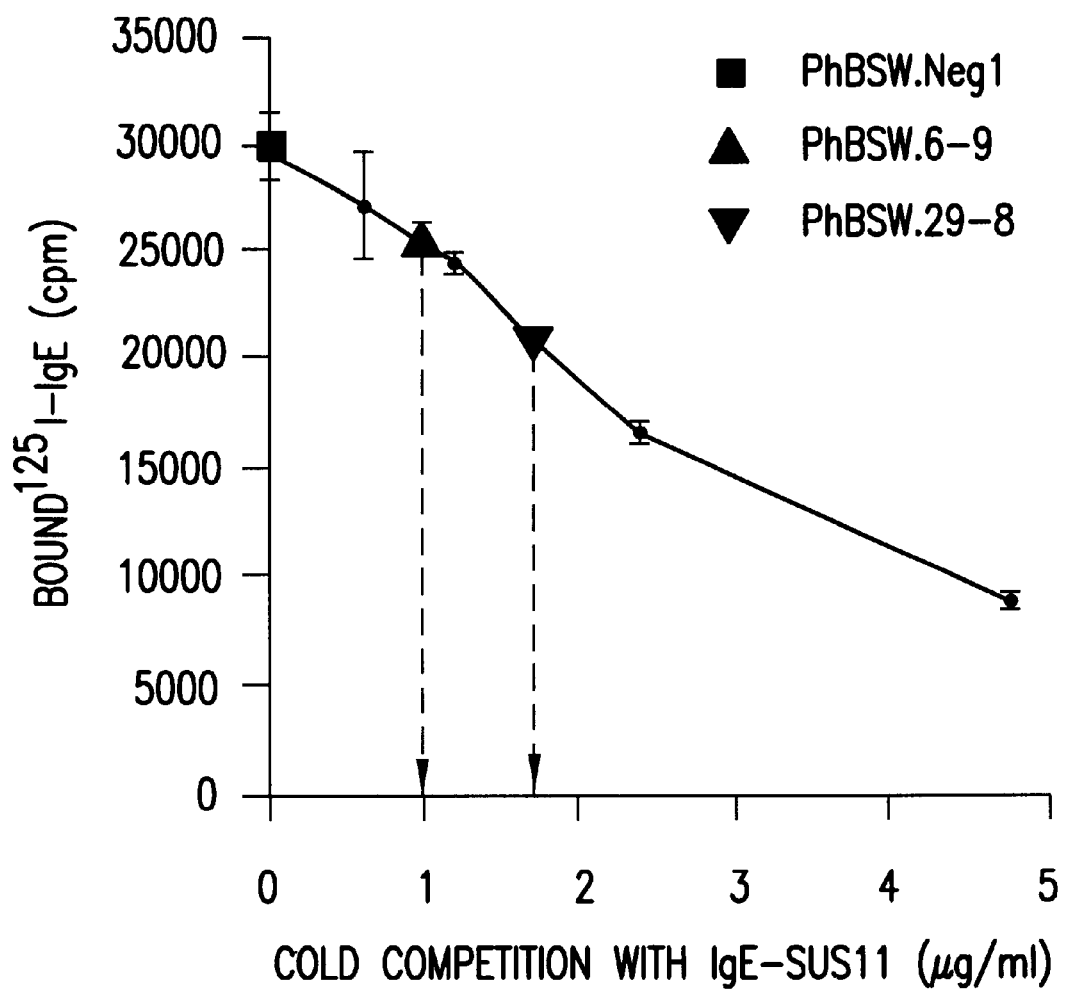
FIG. 6: Phage-displayed BSW17 mimotopes inhibit IgE/BSW17 binding

Mimotope phages (PhBSW.6-9 in FIG. 6=clone 1 of FIG. 5=CRRHNYGFWVC=Seq.id.no. 18; PhBSW.29-8 in FIG. 6=clone 18 of FIG. 5=CINHRGYWVC=Seq.id.no. 19) (see Example 4 above) inhibit the binding of BSW17 to IgE. FIG. 6 shows the binding of $^{125}$I-labelled IgE to BSW17 in the presence of BSW17 mimotope-displaying phage clones. Closed circles show a standard inhibition curve by unlabelled IgE to allow an estimation of inhibition of labeled IgE binding in the presence of $10^{11}$ cfu/ml of phage particles. The inhibition achieved with the phage clones is equal to non-labelled IgE concentrations of 1 µg/ml and 1.7 µg/ml, respectively.

Example 6
Induction of an Epitope-specific Immune Reaction by Immunization of Rabbits With Mimotope-displaying Phase Clones To test the feasibility of a BSW17 mimotope-based vaccine approach, rabbits are immunized with phage particles displaying BSW17 mimotope peptides and helper phage VCS M13 as control, respectively. $10^{12}$ cfu of freshly prepared phage particles are dialyzed against PBS at 4°. 1 ml is emulsified with complete Freund's adjuvant for the first immunization, or with 1 ml incomplete Freund's adjuvant for boosting. Immunization is repeated subcutaneously every 14 days. After the third boost, 12 ml of blood are taken, clotted for 4 hours at room temperature in glass vials and centrifuged for 10 minutes at 2000 g. The supernatants are tested for the presence of anti-human IgE antibodies by ELISA. Human IgE from three different individuals (SUS11-IgE; PS-IgE; WT-IgE) is diluted in PBS at a concentration of 50 µg/ml and 1 µl aliquots are dotted onto nitrocellulose. Nitrocellulose is blocked in TBS containing 1.5% casein for 1 hour. Rabbit serum is diluted 1:200 in TBS containing 1.5% casein and incubated overnight. Washing is performed in TBS, TBS-0.05% Tween 20 and TBS for 10 minutes each. Developing goat anti-rabbit-HRP is 1:1.000 diluted in TBS containing 1.5% casein and incubated for 4 hours. Washing and staining is performed as described. As shown in Table 3, the control rabbits immunized with VCS M13 phage, as well as the non-immunized rabbits show a weak reaction against human IgE in their sera, presumably reflecting naturally occuring anti-rabbit IgE autoantibodies crossreacting with human IgE. However, in addition to a massive immune response to the bacteriophage pVIII coat protein, sera of rabbits immunized with BSW17 mimotope phages also contain strongly elevated levels of antibodies which specifically recognize human IgE:

TABLE 3

Anti-IgE response in rabbits immunized with BSW17 mimotope displaying phage

| | Recognition of IgE (relative OD) | | |
|---|---|---|---|
| Rabbit serum | SUS11-IgE | PS-IgE | WT-IgE |
| nonimmune | 2.0 ± 0.3 | 2.0 ± 0.2 | 2.0 ± 1.0 |
| VCS M13 helper phage | 2.0 ± 0.6 | 2.0 ± 1.0 | 3.0 ± 0.5 |
| PhBSW.6-9 (= clone 1) | 5.0 ± 0.2 | 8.0 ± 0.6 | 21.0 ± 1.0 |
| PhBSW.29-8 (= clone 18) | 16.5 ± 0.7 | 9.0 ± 0.4 | 25.0 ± 1.0 |

BSW17 epitope specificity of these antisera can be demonstrated in a competition ELISA: nitrocellulose strips are prepared as described above and incubated with rabbit serum at a dilution of 1:50 in TBS containing 1.5% casein overnight. After washing, mAb BSW17 labeled with horseradish peroxidase (BSW17-HRP) is added in a 1:50000 dilution in TBS containing 1.5% casein for 4 hours. Subsequent washing and staining is performed as described. As can be seen from Table 4, the binding of BSW17-HRP to IgE preparations from various sources is inhibited by sera from the rabbits immunized with BSW17 mimotope phages, while serum from rabbits immunized with helper phage do not show any inhibitory effect:

TABLE 4

Inhibition of BSW17/IgE interaction with sera of rabbits immunized with BSW17 mimotope phages

| | Recognition of different IgE (% inhibition) | | | |
|---|---|---|---|---|
| | SUS11-IgE | WT-IgE | PS-IgE | Zavasal-IgE |
| VCS M13 helper phage | 0 | 0 | 0 | 0 |
| PhBSW.6-9 | 34 | 65 | 63 | 51 |
| PhBSW.29-8 | 52 | 65 | 48 | 47 |

In the following Examples 7 and 8, the feasibility of using chemically synthesized mimotope peptides coupled to carrier protein as immunogen for the preparation of an antiallergy vaccine is shown:

Example 7
A Chemically Synthesized BSW17 Mimotope Peptide Binds to BSW17 With High Affinity To confirm that the bacteriophage-derived portion of the BSW17 mimotope phages can be omitted without destroying the biological activity of the mimotope peptide sequence, the following peptide is chemically synthesized, comprising the cyclic BSW17 mimotope octapeptide (A) [shown in linear form in Table 2, Group A, second clone as peptide (A) with two additional Cys (Seq.id.no,. 19), and containing here the 7 additional adjacent bacteriophage-derived amino acid residues Gly-Glu-Phe- and -Gly-Asp-Pro-Ala SEQ ID NO.34 as flanking sequences included to facilitate correct folding of the circular mimotope peptide]:

Gly-Glu-Phe-Cys-Ile-Asn-His-Arg-Gly-Tyr-Trp-Val-Cys-Gly-Asp-Pro-Ala (Seq.id.no. 27)

After synthesis by standard technique this peptide is cyclized via the two cysteines and fluorescence-labelled with Rhodol Green. Binding to increasing concentrations of BSW17 immobilized in microtiter plate wells under ELISA conditions is determined by fluorescence measurement and is shown in FIG. 7.

Example 8
Chemically Synthesized BSW17 Mimotope Peptides Coupled to a Carrier Protein are Specifically Recognized by BSW17

Various mimotope peptides are chemically synthesized and coupled to immunogenic carrier proteins. The coupling reactions are performed at a 1:1 mass ratio of peptide and carrier protein, following standard procedures (Shan S. Wong, *Chemistry of Protein Conjugation and Cross-linking*, CRC Press [1993]). Conjugates obtained from the following coupling variants are prepared:
glutaraldehyde coupling
DC (dihexylcarbodiimide) coupling
BSS [bis(sulfosuccinimidyl)suberate] coupling
lysine crosslinking The resultant mimotope conjugates are:
(1) P1=linear KTKGSGFFVF-BSA SEQ ID NO.28 (glutaraldehyde)
(2) P4=linear AcINHRGYWVC-BSA SEQ ID NO.29 (DC)
(3) P5=linear AcRSRSGGYWLWC-BSA SEQ ID NO.36 (DC)
(4) SAF1-KLH=cyclic GEFCINHRYWVCGDPA-KLH SEQ ID NO.33 (DC)

(5) SAF2-KLH=linear KTKGSGFFVF-KLH SEQ ID NO.36 (DC)
(6) SAF3-KLH=linear VNLPWSFGLE-KLH SEQ ID NO.37 (DC)
(7) SAF3-Lys=linear VNLPWSFGLE-lysine crosslinking
(8) SAF4-KLH=linear VNLTWSRASG-KLH SEQ ID NO.38 (DC)
(9) SAF5-KLH=VNLTWS-KLH SEQ ID NO.39 (DC)
(10) SDS214=cyclic GEFCRRHNYGFWVCGDPA-KLH SEQ ID NO.40 (BSS)
(11) SDS213, SDS227, SDS236, SDS252=cyclic GEFCINHRGYWVCGDPA-KLH SEQ ID NO.35 (BSS)
(12) SDS237, SDS253=linear KTKGSGFFVF-KLH SEQ ID NO.36 (BSS)
(13) SDS242, SDS254=linear VNLPWSFGLE-KLH SEQ ID NO.37 (BSS) and
(14) SDS243=linear VNLTWSRASG-KLH SEQ ID NO.38 (BSS), whereby (1), (5) and (12) are reference immunogen molecules prepared by, respectively, glutaraldehyde, DC and BSS coupling; thus:

(1), i.e. P1, is amino acids 500–509 of the human IgE, Seq.id.no. 28, see *The Lancet* [1990] supra, coupled to BSA by glutaraldehyde coupling;

(5), i.e. SAF2-KLH, is that same peptide, Seq.id.no. 28, coupled to KLH by DC coupling; and (12), i.e. SDS237 and SDS253, is that same peptide, Seq.id.no. 28, coupled to KLH by BSS coupling.

The other peptides are immunogens of the invention, namely:

(2) (P4) is N-acetylated peptide (A) (Seq.id.no. 1) with an additional Cys at the C-terminus (Seq.id.no. 29), coupled to BSA by DC coupling;

(3) (P5) is N-acetylated peptide (C) (Seq.id.no. 3) with an additional Cys at the C-terminus (Seq.id.no. 30), coupled to BSA by DC coupling;

(4) (SAF1-KLH) is the peptide of Example 7 (Seq.id.no. 31), cyclized via a disulfide bridge formed by the two flanking Cys, and coupled to KLH by DC coupling;

(6) (SAF3-KLH) is peptide (G) (Seq.id.no. 7), coupled to KLH by DC coupling;

(7) (SAF3-Lys) is peptide (G) (Seq.id.no. 7), coupled by lysine crosslinking;

(8) (SAF4-KLH) is peptide (D) (Seq.id.no. 4), coupled to KLH by DC coupling;

(9) (SAF5-KLH) is peptide (Q) (Seq.id.no. 17) coupled to KLH by DC coupling;

(10) (SDS214) is the first peptide of group A in Table 2, with the same 7 adjacent bacteriophage-derived amino acid residues as the peptide in Example 7 (Seq.id.no. 32), cyclized, and coupled to KLH by BSS coupling;

(11) (SDS213, SDS227, SDS236, SDS252) is the same peptide as (4) above (Seq.id.no. 31), cyclized, and coupled to KLH by BSS coupling;

(13) (SDS242, SDS254) is peptide (G) (Seq.id.no. 7), coupled to KLH by BSS coupling; and

(14) (SDS243) is peptide (D) (Seq.id.no. 4), coupled to KLH by BSS coupling.

FIG. 8a shows that both the cyclic BSW17 mimotope-KLH (BSS) conjugate (11), i.e. SDS236, and the Fcε-derived "original" epitope motif (12), i.e. SDS237, i.e. Fcε (500–509) coupled as linear peptide to KLH (BSS), are recognized by BSW17 in a dose-dependent manner, while free KLH shows no binding. Microtiter plate wells are coated with 1 μg each of SDS236, SDS237 or free KLH and incubated with increasing concentrations of BSW17. Bound antibody is detected with goat anti-mouse IgG-HRP (gamIgG-HRP). The data shown represents means of duplicates minus background binding to uncoated (BSA-blocked) wells.

FIG. 8b summarizes ELISA data obtained with various BSW17 mimotope conjugates coupled to the carrier protein using several chemical coupling procedures. Microtiter plate wells are coated with 5 μg each of the mimotope conjugates, or free KLH, and incubated with 10 μg of BSW17. Bound antibody is detected with gamIgG-HRP. The data shown represents means of duplicates minus background binding to uncoated (BSA-blocked) wells. In contrast to free KLH, each BSW17 mimotope conjugate is found to be recognized by BSW17. However, from repeated experiments carried out over several weeks it becomes clear that the KLH conjugates coupled via DC are less stable and gradually lose their binding capacity for BSW17. In contrast, BSW17 mimotope conjugates obtained by BSS coupling prove to be stable even at +4°.

In FIGS. 9a and 9b it is shown that BSW17 mimotopes coupled to KLH or BSA are specifically recognized by BSW17 and not by the non-related monoclonal antibodies 3G9 (anti-human Cε3) and 5H5/F8 (anti-human RIα). Again, microtiter plate wells are coated with 5 μg each of the mimotope conjugates shown and incubated with 10 μg of the corresponding monoclonal antibody. Bound antibody is detected with gamIgG-HRP. The data shown represents means of duplicates minus background binding to uncoated (BSA-blocked) wells.

Example 9
Immunization of Rabbits with BSW17 Mimotope Conjugates Results in the In Vivo Generation of Anti Human IgE Antibodies To confirm the specificity of the immunogenicity of the BSW17 mimotope conjugates, rabbits are immunized with a set of mimotope/carrier preparations as outlined below:

| Rabbit No. | Immunogen | Conjugate type |
|---|---|---|
| R1 | (10) SDS214 | |
| R2 | (10) SDS214 | Cε4 mimotopes |
| R3 | (11) SDS213 | |
| R4 | (11) SDS213 | |
| 1 | KLH (Pierce) | |
| 2 | KLH-BSS linker | KLH control |
| 4 | (12) SDS237 | |
| 11 | (12) SDS237 | Cε4 (500–509) |
| 7 | (6) SAF3-KLH | |
| 13 | (7) SAF3-Lys | |
| 14 | (13) SDS242 | Cε3 mimotope |
| 16 | (13) SDS242 | |
| 17 | (13) SDS254 | |
| 18 | (7) SAF3-Lys | |
| 5 | (8) SAF4-KLH | Cε3 (370–379) |
| 8 | (8) SAF4-KLH | |
| 19 | (14) SDS243 | |
| 20 | (14) SDS243 | |
| 12 | (4) SAF1-KLH | |
| 15 | (4) SAF1-KLH | Cε4 mimotope |

Rabbits are immunized with 200 μg of the corresponding conjugate preparation dissolved in a total volume of 500 μl of phosphate-buffered saline (PBSdef.) by s.c. injection. For the first immunization samples are mixed 1:1 with complete Freund's adjuvant (rabbits R1–R4) TITERMAX® (Sigma;

rabbits 1–20). Prior to the initial immunization, 5 ml of blood samples are taken. Boosting is performed on days 21 and 28 after the first injection using incomplete Freund's adjuvant. Blood samples are taken on day 28 and 49 and serum is prepared from all samples.

The generation of an anti-human IgE immune response in the immunized rabbits is monitored by ELISA: microtiter plate wells are coated with 5 µg of human IgE (SUS-11; JW8) and incubated with 100 µl of serum samples, diluted 1:50 with ELISA incubation buffer. Rabbit antibodies bound by the immobilized human IgE are detected by incubation with goat anti-rabbit IgG-HRP (garIgG-HRP). The measured $OD_{405}$ values are corrected by the read-out obtained with pre-immune serum from each corresponding rabbit, diluted 1:50. The data given in FIGS. 10a and 10b represents mean values of duplicate measurements. FIGS. 10a and 10b clearly demonstrate the induction of antibodies in rabbits immunized with various BSW17 mimotope conjugates which are directed against human IgE.

Serum titers of the newly generated antibodies with respect to the KLH carrier, the peptide used as immunogen and human IgE, respectively, are also determined by ELISA, using serial serum dilutions for incubation with immobilized KLH, mimotope peptide-BSA conjugate and human IgE, respectively. Two examples of such serum titer determinations are shown in FIG. 11, for(11), i.e. SDS 213, and for (10), i.e. SDS 214, respectively.

The above Example demonstrates the applicability of BSW17 mimotope conjugates as immunogens for the induction of an anti-human IgE response.

Example 10

Figure 12:
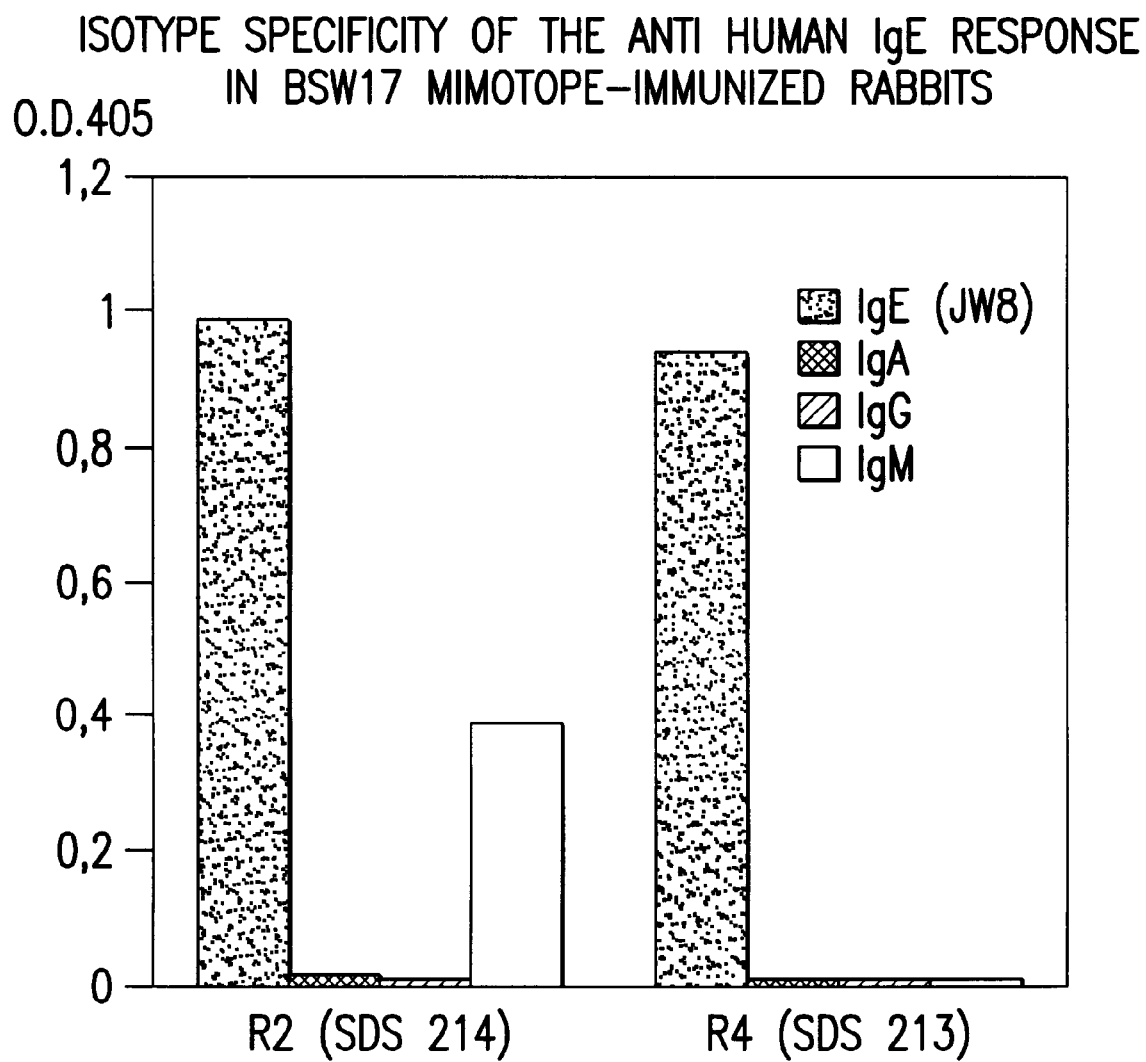
FIG. 12: Isotype specificity of the anti-human IgE response in BSW17 mimotope-immunized rabbits

The Anti-hIgE Response Induced in Rabbits Immunized With BSW17 Mimotope Conjugates is Isotype-specific and Competes With BSW17 for IgE Binding The isotype specificity of the anti-human IgE immune response in the immunized rabbits is monitored by ELISA: microtiter plate wells are each coated with 3 µg of human IgE (SUS-11), IgA, IgG, and IgM, respectively, and incubated with 100 µl of serum samples, diluted 1:50 with ELISA incubation buffer. Rabbit antibodies bound by the immobilized human antibodies are detected by incubation with goat garIgG-HRP. The measured $OD_{405}$ values are corrected by the read-out obtained with 1:50 diluted preimmune serum of each corresponding rabbit, diluted 1:50. The data given in FIG. 12 represents mean values of duplicate measurements. As can be seen, the immune response generated in rabbits by immunization with BSW17 mimotope conjugates is specific for IgE, apart from a partial recognition of human IgM by the serum of the rabbit immunized with (10), i.e. SDS214.

In a competition ELISA it is further shown that rabbit anti-SDS214 antiserum is able to partially compete with BSW17, for IgE binding. Microtiter plate wells are each coated with 1 µg of human IgE (SUS-11) and either incubated with 5 µg of BSW17 or incubation buffer without BSW17. After washing, 100 µl of anti-SDS213 antiserum, diluted 1:50 with ELISA incubation buffer, is added for a second incubation. Rabbit antibodies bound by untreated immobilized human IgE and IgE preincubated with BSW117 are detected by incubation with goat garIgG-HRP. The data given in FIG. 13 represent mean values of duplicate measurements.

Example 11

The Anti-hIgE Antibodies Generated in Rabbits by Immunization With BSW17 Mimotope Conjugates can be Purified by Affinity Chromatography Using Mimotope Peptide Coupled to Sepharose as Affinity Reagent This Example demonstrates that the anti-hIgE response induced in rabbits by immunization with BSW17 mimotope conjugates is identical with the specific anti-mimotope peptide response.

Immunoaffinity purification of rabbit polyclonal anti-BSW17 mimotope antibodies:

a) Ammonium Sulfate Precipitation:

To 22 ml of rabbit antiserum (60 mg/ml of total protein according to Bradford, BSA-Standard, BIO-RAD) 5.5 g of solid AMS (25% w/v) is added, the mixture is stirred for 3 hours and incubated overnight at room temperature. The precipitate is removed by centrifugation at 18000 rpm (Sorvall) for 45 minutes and washed with 25 ml of 25% AMS aqueous solution (w/v). The washed precipitate is centrifuged again under the same conditions, dissolved in 10 ml of PBS, 0.05% $NaN_3$, pH 7.2, and dialysed against 5 l of the same buffer overnight at +4°.

b) Immunoaffinity Chromatography:

The dialysate is filtered on a 0.2 µm MILLEX® -GV filter unit (Millipore) and applied to a Pharmacia XK16/30 column filled with 10 ml of CH-Sepharose 4B covalently coupled to 5 mg of BSW17 mimotope peptide SDS227 at a flow rate of 1 ml/min with PBS, 0.05% $NaN_3$ as running buffer. After application and elution of the unbound protein fraction, specifically bound antibody is eluted with 0.1 M glycine/HCl buffer pH 2.8. The eluate (fractions #12–20 in 9 ml) is trapped under stirring for immediate neutralization to pH 7.4 with 3.3 M TRIS/HAc, 0.8% $NaN_3$ pH 8.0 (50 µl/ml) and finally dialysed against 3 l of PBS, 0.05% NaN3, pH 7.2 overnight at 4°. Total protein is about 1 mg/ml according to Bradford, BIgG Standard (BIO-RAD). The recovery from total protein applied is about 0.7%.

Figure 14:
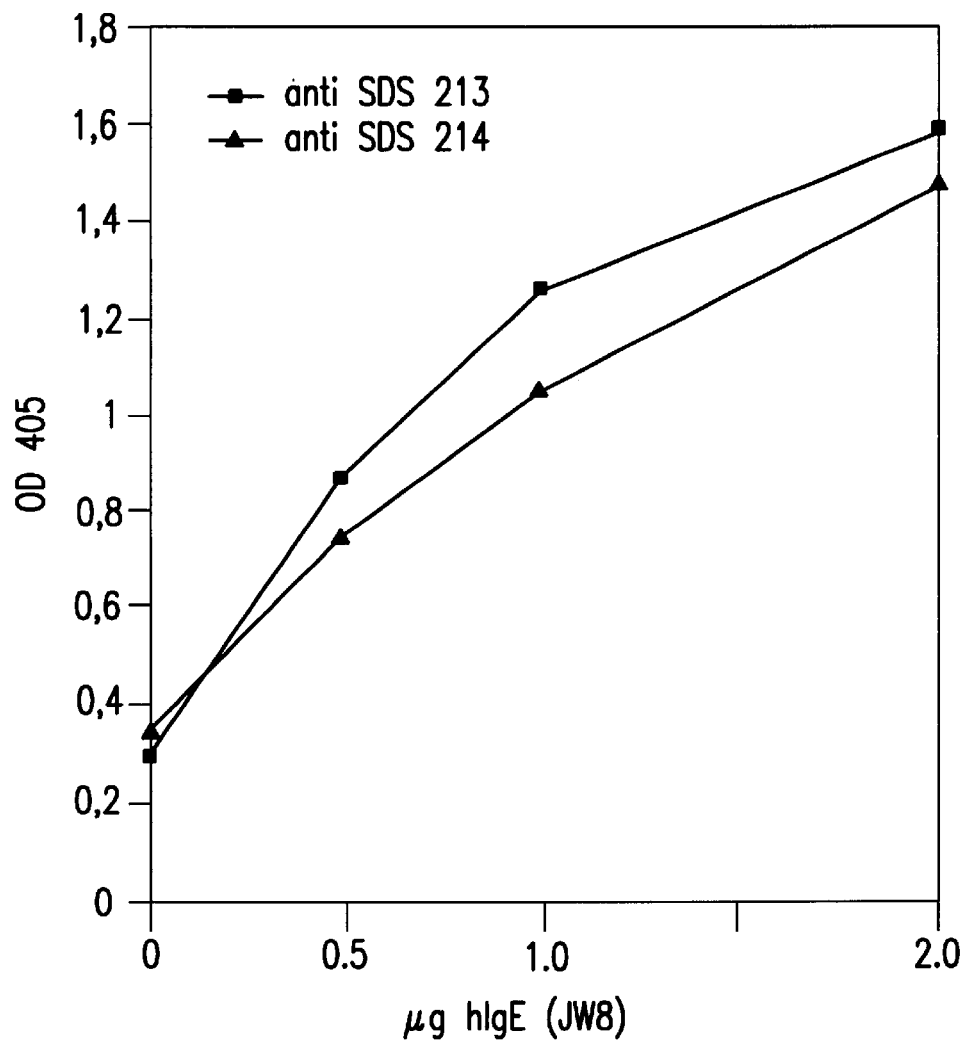
FIG. 14: Binding of affinity-purified anti BSW17 mimotope antibodies to hIgE

Affinity-purified IgG fractions are tested for hIgE binding by ELISA. Microtiter plate wells are coated with increasing concentrations of human IgE (JW8) and incubated with 5 µg of the purified anti-SDS-213 antiserum and anti SDS-214 antiserum, respectively. Bound antibody is detected with garIgG-HRP. The data shown in FIG. 14 represents mean values of duplicates. As can be seen from the Figure, the IgG antibodies purified on the anti-BSW17 mimotope affinity column are dose-dependently recognized by human IgE. Only low background binding activity is observed with samples of the column flow through. This data demonstrates that the anti-hIgE activity induced in the rabbits is identical with the antibodies directed against the mimotope peptide.

Example 12

The Anti Human IgE Antibodies Generated in Rabbits After Immunization With BSW17 Mimotope Conjugates are Non-anaphylactogenic on Human Blood Cells It is shown here that the anti-IgE antibodies generated in rabbits by immunization with BSW17 mimotope conjugates are non-anaphylactogenic on human blood basophils. As test system, the commercially available CAST sLt ELISA kit (Bühlmann AG, Allschwil, Switzerland) is used. In this assay the release of soluble leukotriene (sLt) from human basophils as a consequence of triggering the cells by anaphylactogenic agents is determined following the experimental protocol provided by the supplier. The read-out of the assay is given as pg sLt present per ml of human white blood cell supernatant after incubation of the cells with the test sample, as determined by comparison with a standard curve. The standard curve is obtained using a serial dilution of standard sLt in a competition ELISA. sLt background levels resulting from spontaneous sLt release from the blood cell preparation (PB="patient blank") and maximum sLt that can be released from a given blood cell preparation (PC="patient control"; obtained after triggering of the cell samples with a crosslinking anti-IgERIα antibody) are included in each test as negative and positive controls, respectively.

Figure 15:
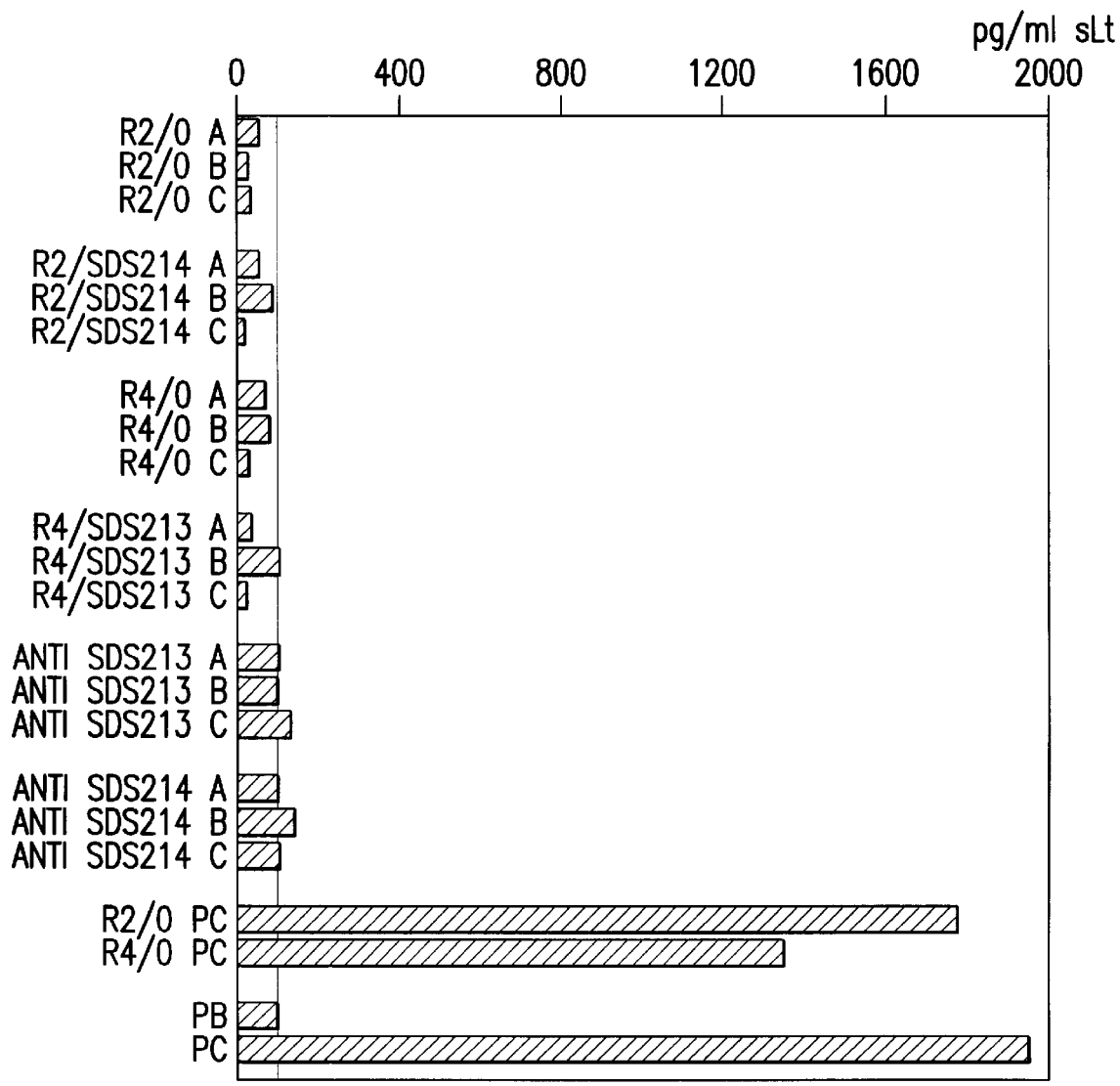
FIG. 15: Test of rabbit anti BSW17 mimotope sera and affinity-purified anti BSW17 mimotope antibodies for anaphylactogenicity on human blood cells.

Complete sera from rabbits immunized with BSW17 mimotope conjugates as well as the affinity-purified anti-BSW17 mimotope antibodies described in Example 11 are tested for the presence of basophil triggering and thus for anaphylactogenic anti-hIgE antibodies. As source for basophils, freshly taken whole human blood of a healthy donor is used and processed strictly according to the protocol of the CAST ELISA kit. The results are summarized in FIG. 15 and show that neither non-purified rabbit serum containing the anti-hIgE antibodies generated by immunization with BSW17 mimotope conjugates, nor the affinity-purified anti-BSW17 mimotope antibodies, have the capability of triggering human blood cells for leukotriene release; they are thus non-anaphylactogenic. This is an absolute prerequisite for the application of BSW17 mimotopes in a human anti-allergy vaccine.

What is claimed is:

1. An immunogenic molecule comprising
   (a) at least one mimotope peptide-comprising moiety which comprises a mimotope peptide of up to 15 amino acids, said peptide being a mimotope of the monoclonal antibody produced by the hybridoma cell line deposited under European Collection of Cell Cultures deposit number 96121916, wherein the mimotope peptide is not Lys-Thr-Lys-Gly-Ser-Gly-Phe-Phe-Val-Phe (SEQ ID NO:28); and
   (b) an immunogenic carrier moiety.

2. An immunogenic molecule according to claim 1 wherein the mimotope peptide-comprising moiety comprises an amino acid sequence selected from the group consisting of:
   Ile-Asn-His-Arg-Gly-Tyr-Trp-Val (A) (SEQ ID NO:1),
   Arg-Asn-His-Arg-Gly-Tyr-Trp-Val (B) (SEQ ID NO:2),
   Arg-Ser-Arg-Ser-Gly-Gly-Tyr-Trp-Leu-Trp (C) (SEQ ID NO:3),
   Val-Asn-Leu-Thr-Trp-Ser-Arg-Ala-Ser-Gly (D) (SEQ ID NO:4),
   Val-Asn-Leu-Pro-Trp-Ser-Arg-Ala-Ser-Gly (E) (SEQ ID NO:5),
   Val-Asn-Leu-Thr-Trp-Ser-Phe-Gly-Leu-Gly (F) (SEQ ID NO:6),
   Val-Asn-Leu-Pro-Trp-Ser-Phe-Gly-Leu-Gly (G) (SEQ ID NO:7),
   Val-Asn-Arg-Pro-Trp-Ser-Phe-Gly-Leu-Gly (H) (SEQ ID NO:8),
   Val-Lys-Leu-Pro-Trp-Arg-Phe-Tyr-Gln-Val (I) (SEQ ID NO:9),
   Val-Trp-Thr-Ala-Cys-Gly-Tyr-Gly-Arg-Met (J) (SEQ ID NO:10),
   Gly-Thr-Val-Ser-Thr-Leu-Ser (K) (SEQ ID NO:11),
   Leu-Leu-Asp-Ser-Arg-Tyr-Trp (L) (SEQ ID NO:12),
   Gln-Pro-Ala-His-Ser-Leu-Gly (M) (SEQ ID NO:13),
   Leu-Trp-Gly-Met-Gln-Gly-Arg (N) (SEQ ID NO:14),
   Leu-Thr-Leu-Ser-His-Pro-His-Trp-Val-Leu-Asn-His-Phe-Val-Ser (O) (SEQ ID NO:15),
   Ser-Met-Gly-Pro-Asp-Gln-Thr-Leu-Arg (P) (SEQ ID NO:16), and
   Val-Asn-Leu-Thr-Trp-Ser (Q) (SEQ ID NO:17).

3. The immunogenic molecule of claim 1, wherein the mimotope peptide-comprising moiety further comprises a cysteine residue attached to the amino terminal amino acid of the mimotope peptide and a cysteine residue attached to the carboxyl terminal amino acid of the mimotope peptide, wherein the cysteine residues form a disulfide bond.

4. The immunogenic molecule of claim 1, wherein the mimotope peptide is linear and comprises an acetyl group bonded to the amino terminal amino acid, an amidated carboxyl terminal amino acid, or both an acetyl group bonded to the amino terminal amino acid and an amidated carboxyl terminal amino acid.

5. The immunogenic molecule of claim 1, wherein the mimotope peptide-comprising moiety further comprises one or more members independently selected from the group consisting of coupling groups and ancillary groups, wherein the coupling groups and ancillary groups are covalently bonded to the mimotope peptide.

6. The immunogenic molecule of claim 1, wherein the mimotope peptide-comprising moiety is covalently bound to the immunogenic carrier moiety through a peptide bond.

7. The immunogenic molecule of claim 1, wherein the mimotope peptide-comprising moiety is covalently bound to the immunogenic carrier moiety through a coupling group.

8. The immunogenic molecule of claim 1, wherein the mimotope peptide-comprising moiety is a peptide with the amino acid' sequence set forth in SEQ ID NO:27, wherein the cysteine residues of said peptide-comprising moiety form a disulfide bond.

9. A composition comprising an immunogenic molecule according to claim 1.

10. A ligand comprising an antibody domain reactive with a mimotope peptide-comprising moiety as defined in claim 1, wherein said antibody domain is also reactive with the sequence of amino acids on the heavy chain of IgE that comprise the natural epitope recognized by the monoclonal antibody produced by the hybridoma cell line deposited under European Collection of Cell Cultures deposit number 96121916.

11. The immunogenic molecule according to claim 3 wherein the mimotope peptide-comprising moiety comprises the amino acid sequence Cys-Ile-Asn-His-Arg-Gly-Tyr-Trp-Val-Cys (SEQ ID NO:19) and hapten-binding components, wherein the cysteine residues of said mimotope peptide form a disulfide bond.

12. The immunogenic molecule of claim 3, wherein the mimotope peptide-comprising moiety further comprises a glycine-glutamate-phenylalanine moiety attached through the phenylalanine to the cysteine residue attached to the amino terminal amino acid of the mimotope peptide, and a glycine-aspartate moiety attached through the glycine to the cysteine residue attached to the carboxyl terminal amino acid of them mimotope peptide, wherein the cysteine residues form a disulfide bond.

13. The composition of claim 9 which further comprises an adjuvant.

14. The peptide Ile-Asn-His-Arg-Gly-Tyr-Trp-Val (SEQ ID NO:1).

15. A peptide selected from the group consisting of
Arg-Asn-His-Arg-Gly-Tyr-Trp-Val (B) (SEQ ID NO:2),
Arg-Ser-Arg-Ser-Gly-Gly-Tyr-Trp-Leu-Trp (C) (SEQ ID NO:3),
Val-Asn-Leu-Thr-Trp-Ser-Arg-Ala-Ser-Gly (D) (SEQ ID NO:4),
Val-Asn-Leu-Pro-Trp-Ser-Arg-Ala-Ser-Gly (E) (SEQ ID NO:5),
Val-Asn-Leu-Thr-Trp-Ser-Phe-Gly-Leu-Gly (F) (SEQ ID NO:6),
Val-Asn-Leu-Pro-Trp-Ser-Phe-Gly-Leu-Gly (G) (SEQ ID NO:7),
Val-Asn-Arg-Pro-Trp-Ser-Phe-Gly-Leu-Gly (H) (SEQ ID NO:8),
Val-Lys-Leu-Pro-Trp-Arg-Phe-Tyr-Gln-Val (I) (SEQ ID NO:9),
Val-Trp-Thr-Ala-Cys-Gly-Tyr-Gly-Arg-Met (J) (SEQ ID NO:10),
Gly-Thr-Val-Ser-Thr-Leu-Ser (K) (SEQ ID NO:11),
Leu-Leu-Asp-Ser-Arg-Tyr-Trp (L) (SEQ ID NO:12),
Gln-Pro-Ala-His-Ser-Leu-Gly (M) (SEQ ID NO:13),
Leu-Trp-Gly-Met-Gln-Gly-Arg (N) (SEQ ID NO:14),
Leu-Thr-Leu-Ser-His-Pro-His-Trp-Val-Leu-Asn-His-Phe-Val-Ser (O) (SEQ ID NO:15),
Ser-Met-Gly-Pro-Asp-Gln-Thr-Leu-Arg (P) (SEQ ID NO:16), and
Val-Asn-Leu-Thr-Trp-Ser (Q) (SEQ ID NO:17).

16. A mimotope peptide of up to 15 amino acids, said mimotope peptide being a mimotope of the monoclonal antibody produced by the hybridoma cell line deposited under European Collection of Cell Cultures deposit number 96121916, said mimotope peptide comprising an amino acid sequence selected from the group consisting of:
Ile-Asn-His-Arg-Gly-Tyr-Trp-Val (A) (SEQ ID NO:1),
Arg-Asn-His-Arg-Gly-Tyr-Trp-Val (B) (SEQ ID NO:2),
Arg-Ser-Arg-Ser-Gly-Gly-Tyr-Trp-Leu-Trp (C) (SEQ ID NO:3),
Val-Asn-Leu-Thr-Trp-Ser-Arg-Ala-Ser-Gly (D) (SEQ ID NO:4),
Val-Asn-Leu-Pro-Trp-Ser-Arg-Ala-Ser-Gly (E) (SEQ ID NO:5),
Val-Asn-Leu-Thr-Trp-Ser-Phe-Gly-Leu-Gly (F) (SEQ ID NO:6),
Val-Asn-Leu-Pro-Trp-Ser-Phe-Gly-Leu-Gly (G) (SEQ ID NO:7),
Val-Asn-Arg-Pro-Trp-Ser-Phe-Gly-Leu-Gly (H) (SEQ ID NO:8),
Val-Lys-Leu-Pro-Trp-Arg-Phe-Tyr-Gln-Val (I) (SEQ ID NO:9),
Val-Trp-Thr-Ala-Cys-Gly-Tyr-Gly-Arg-Met (J) (SEQ ID NO:10),
Gly-Thr-Val-Ser-Thr-Leu-Ser (K) (SEQ ID NO:11),
Leu-Leu-Asp-Ser-Arg-Tyr-Trp (L) (SEQ ID NO:12),
Gln-Pro-Ala-His-Ser-Leu-Gly (M) (SEQ ID NO:13),
Leu-Trp-Gly-Met-Gln-Gly-Arg (N) (SEQ ID NO:14),
Leu-Thr-Leu-Ser-His-Pro-His-Trp-Val-Leu-Asn-His-Phe-Val-Ser (O) (SEQ ID NO:15),
Ser-Met-Gly-Pro-Asp-Gln-Thr-Leu-Arg (P) (SEQ ID NO:16), and
Val-Asn-Leu-Thr-Trp-Ser (Q) (SEQ ID NO:17).

* * * * *

```
                          SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:1:

Ile Asn His Arg Gly Tyr Trp Val
1               5

(2) INFORMATION FOR SEQ ID NO:2:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:2:

Arg Asn His Arg Gly Tyr Trp Val
1               5

(2) INFORMATION FOR SEQ ID NO:3:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (iii) HYPOTHETICAL: YES (iv) ANTI-SENSE: NO (v) FRAGMENT TYPE: internal
```

(xi) SEQUENCE DESCRIPTION: SEQ ID NO:3:

Arg Ser Arg Ser Gly Gly Tyr Trp Leu Trp
1               5                   10

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:4:

Val Asn Leu Thr Trp Ser Arg Ala Ser Gly
1               5                   10

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:5:

Val Asn Leu Pro Trp Ser Arg Ala Ser Gly
1               5                   10

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:6:

Val Asn Leu Thr Trp Ser Phe Gly Leu Glu
1               5                   10

(2) INFORMATION FOR SEQ ID NO:7:

(i) SEQUENCE CHARACTERISTICS:
        (A) LENGTH: 10 amino acids
        (B) TYPE: amino acid
        (C) STRANDEDNESS: single

```
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:7:

Val Asn Leu Pro Trp Ser Phe Gly Leu Glu
1               5                   10

(2) INFORMATION FOR SEQ ID NO:8:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:8:

Val Asn Arg Pro Trp Ser Phe Gly Leu Glu
1               5                   10

(2) INFORMATION FOR SEQ ID NO:9:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:9:

Val Lys Leu Pro Trp Arg Phe Tyr Gln Val
1               5                   10

(2) INFORMATION FOR SEQ ID NO:10:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:10:

Val Trp Thr Ala Cys Gly Tyr Gly Arg Met
```

```
1               5          10
```

(2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:11:

```
Gly Thr Val Ser Thr Leu Ser
1               5
```

(2) INFORMATION FOR SEQ ID NO:12:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:12:

```
Leu Leu Asp Ser Arg Tyr Trp
1               5
```

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:13:

```
Gln Pro Ala His Ser Leu Gly
1               5
```

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:14:

```
Leu Trp Gly Met Gln Gly Arg
1               5
```

(2) INFORMATION FOR SEQ ID NO:15:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:15:

```
Leu Thr Leu Ser His Pro His Trp Val Leu Asn His Phe Val Ser
1               5                   10                  15
```

(2) INFORMATION FOR SEQ ID NO:16:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:16:

```
Ser Met Gly Pro Asp Gln Thr Leu Arg
1               5
```

(2) INFORMATION FOR SEQ ID NO:17:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:17:

```
Val Asn Leu Thr Trp Ser
1               5
```

(2) INFORMATION FOR SEQ ID NO:18:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:18:

Cys Arg Arg His Asn Tyr Gly Phe Trp Val Cys
1               5                   10

(2) INFORMATION FOR SEQ ID NO:19:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:19:

Cys Ile Asn His Arg Gly Tyr Trp Val Cys
1               5                   10

(2) INFORMATION FOR SEQ ID NO:20:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:20:

Cys Thr Arg Leu His Thr Gly Tyr Trp Val Cys
1               5                   10

(2) INFORMATION FOR SEQ ID NO:21:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:21:

Cys Thr Leu Ser Val Phe Gly Tyr Trp Val Cys
1               5                   10

(2) INFORMATION FOR SEQ ID NO:22:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:22:

Cys Ser Met Gly Pro Asp Gln Thr Leu Arg Cys
1               5                   10

(2) INFORMATION FOR SEQ ID NO:23:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:23:

Cys Leu Leu Asp Ser Arg Tyr Trp Cys
1               5

(2) INFORMATION FOR SEQ ID NO:24:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:24:

Cys Gln Pro Ala His Ser Leu Gly Cys
1               5

(2) INFORMATION FOR SEQ ID NO:25:

(i) SEQUENCE CHARACTERISTICS:
        (A) LENGTH: 9 amino acids
        (B) TYPE: amino acid (C) STRANDEDNESS: single
          (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:25:

Cys Leu Trp Gly Met Gln Gly Arg Cys
1               5

(2) INFORMATION FOR SEQ ID NO:26:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:26:

Cys Gly Thr Val Ser Thr Leu Ser Cys
1               5

(2) INFORMATION FOR SEQ ID NO:27:

(i) SEQUENCE CHARACTERISTICS:
          (A) LENGTH: 17 amino acids
          (B) TYPE: amino acid
          (C) STRANDEDNESS: single
          (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:27:

Gly Glu Phe Cys Ile Asn His Arg Gly Tyr Trp Val Cys Gly Asp Pro
1               5                  10                  15
Ala (2) INFORMATION FOR SEQ ID NO:28:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: peptide (iii) HYPOTHETICAL: YES (iv) ANTI-SENSE: NO (v) FRAGMENT TYPE: internal

```
        (xi) SEQUENCE DESCRIPTION: SEQ ID NO:28:

Lys Thr Lys Gly Ser Gly Phe Phe Val Phe
1               5                   10

(2) INFORMATION FOR SEQ ID NO:29:

(i) SEQUENCE CHARACTERISTICS:
           (A) LENGTH: 9 amino acids
           (B) TYPE: amino acid
           (C) STRANDEDNESS: single
           (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:29:

Ile Asn His Arg Gly Tyr Trp Val Cys
1               5

(2) INFORMATION FOR SEQ ID NO:30:

(i) SEQUENCE CHARACTERISTICS:
           (A) LENGTH: 11 amino acids
           (B) TYPE: amino acid
           (C) STRANDEDNESS: single
           (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:30:

Arg Ser Arg Ser Gly Gly Tyr Trp Leu Trp Cys
1               5                   10

(2) INFORMATION FOR SEQ ID NO:31:

(i) SEQUENCE CHARACTERISTICS:
           (A) LENGTH: 17 amino acids
           (B) TYPE: amino acid
           (C) STRANDEDNESS: single
           (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:31:

Gly Glu Phe Cys Ile Asn His Arg Gly Tyr Trp Val Cys Gly Asp Pro
1               5                   10                  15
Ala (2) INFORMATION FOR SEQ ID NO:32:

(i) SEQUENCE CHARACTERISTICS:
           (A) LENGTH: 18 amino acids
           (B) TYPE: amino acid
```

```
            (C) STRANDEDNESS: single
            (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:32:

Gly Glu Phe Cys Arg Arg His Asn Tyr Gly Phe Trp Val Cys Gly Asp
1               5                  10                  15

Pro Ala (2) INFORMATION FOR SEQ ID NO:33:

(i) SEQUENCE CHARACTERISTICS:
            (A) LENGTH: 20 amino acids
            (B) TYPE: amino acid
            (C) STRANDEDNESS: single
            (D) TOPOLOGY: circular (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:33:

Gly Glu Phe Cys Ile Asn His Arg Gly Tyr Trp Val Cys Gly Asp Pro
1               5                  10                  15

Ala Lys Leu His
            20

(2) INFORMATION FOR SEQ ID NO:34:

(i) SEQUENCE CHARACTERISTICS:
            (A) LENGTH: 17 amino acids
            (B) TYPE: amino acid
            (C) STRANDEDNESS: single
            (D) TOPOLOGY: circular (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:34:

Cys Ile Asn His Arg Gly Tyr Trp Val Cys Gly Glu Phe Gly Asp Pro
1               5                  10                  15

Ala (2) INFORMATION FOR SEQ ID NO:35:

(i) SEQUENCE CHARACTERISTICS:
            (A) LENGTH: 20 amino acids
            (B) TYPE: amino acid
            (C) STRANDEDNESS: single
            (D) TOPOLOGY: circular (ii) MOLECULE TYPE: peptide (iii) HYPOTHETICAL: YES
```

(iv) ANTI-SENSE: NO (v) FRAGMENT TYPE: internal (xi) SEQUENCE DESCRIPTION: SEQ ID NO:35:

Gly Glu Phe Cys Ile Asn His Arg Gly Tyr Trp Val Cys Gly Asp Pro
1               5                   10                  15

Ala Lys Leu His
            20

(2) INFORMATION FOR SEQ ID NO:36:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:36:

Lys Thr Lys Gly Ser Gly Phe Phe Val Phe Lys Leu His
1               5                   10

(2) INFORMATION FOR SEQ ID NO:37:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:37:

Val Asn Leu Pro Trp Ser Phe Gly Leu Glu Lys Leu His
1               5                   10

(2) INFORMATION FOR SEQ ID NO:38:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:38:

Val Asn Leu Thr Trp Ser Arg Ala Ser Gly Lys Leu His
1               5                   10

(2) INFORMATION FOR SEQ ID NO:39:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:39:

Val Asn Leu Thr Trp Ser Lys Leu His
1               5

(2) INFORMATION FOR SEQ ID NO:40:

(i) SEQUENCE CHARACTERISTICS:
        (A) LENGTH: 21 amino acids
        (B) TYPE: amino acid
        (C) STRANDEDNESS: single
        (D) TOPOLOGY: circular (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:40:

Gly Glu Phe Cys Arg Arg His Asn Tyr Gly Phe Trp Val Cys Gly Asp
1               5                   10                  15

Pro Ala Lys Leu His
            20